United States Patent
Ikeda

(10) Patent No.: US 10,438,811 B1
(45) Date of Patent: Oct. 8, 2019

(54) METHODS FOR FORMING NANO-GAP ELECTRODES FOR USE IN NANOSENSORS

(71) Applicant: Quantum Biosystems Inc., Osaka (JP)

(72) Inventor: Shuji Ikeda, Osaka (JP)

(73) Assignee: QUANTUM BIOSYSTEMS INC., Tokyo (JP)

( * ) Notice: Subject to any disclaimer, the term of this patent is extended or adjusted under 35 U.S.C. 154(b) by 0 days.

(21) Appl. No.: 14/687,856

(22) Filed: Apr. 15, 2015

Related U.S. Application Data

(60) Provisional application No. 61/995,600, filed on Apr. 15, 2014.

(51) Int. Cl.
*H01L 21/311* (2006.01)
*H01L 21/285* (2006.01)
*C12Q 1/6869* (2018.01)

(52) U.S. Cl.
CPC ...... *H01L 21/31138* (2013.01); *C12Q 1/6869* (2013.01); *H01L 21/28568* (2013.01)

(58) Field of Classification Search
CPC ......... H01L 21/31138; H01L 21/28568; C12Q 1/6869
See application file for complete search history.

(56) References Cited

U.S. PATENT DOCUMENTS

| | | |
|---|---|---|
| 5,092,972 A | 3/1992 | Ghowsi |
| 5,122,248 A | 6/1992 | Karger et al. |
| 5,151,164 A | 9/1992 | Blanchard et al. |
| 5,262,031 A | 11/1993 | Lux et al. |
| 5,593,838 A | 1/1997 | Zanzucchi et al. |
| 5,906,723 A | 5/1999 | Mathies et al. |
| 6,159,353 A | 12/2000 | West et al. |
| 6,447,663 B1 | 9/2002 | Lee et al. |
| 6,491,805 B1 | 12/2002 | Gordon et al. |
| 6,613,513 B1 | 9/2003 | Parce et al. |
| 6,905,586 B2 | 6/2005 | Lee et al. |
| 7,033,476 B2 | 4/2006 | Lee et al. |
| 7,468,271 B2 | 12/2008 | Golovchenko et al. |
| 7,892,414 B1 | 2/2011 | Sumner |
| 7,918,979 B2 | 4/2011 | Han et al. |
| 8,105,471 B1 | 1/2012 | Han et al. |

(Continued)

FOREIGN PATENT DOCUMENTS

| | | |
|---|---|---|
| CN | 101046458 A | 10/2007 |
| CN | 101920932 A | 12/2010 |

(Continued)

OTHER PUBLICATIONS

Carter, et al. Voltammetric studies of the interaction of metal chelates with DNA. 2. Tris-chelated complexes of cobalt (III) and iron (II) with 1, 10-phenanthroline and 2, 2'-bipyridine. Journal of the American Chemical Society 111.24 (1989): 8901-8911.

(Continued)

*Primary Examiner* — Julio J Maldonado
*Assistant Examiner* — Hajar Kolahdouzan
(74) *Attorney, Agent, or Firm* — Wilson Sonsini Goodrich & Rosati

(57) ABSTRACT

Methods for forming electrodes for use in nano-gap electrodes are provided. Such methods can be used to form electrodes for use in devices that can be used to sense or detect biomolecules, such as in biomolecule sequence applications.

17 Claims, 10 Drawing Sheets

(56) References Cited

U.S. PATENT DOCUMENTS

| | | |
|---|---|---|
| 8,333,934 B2 | 12/2012 | Cao et al. |
| 8,652,779 B2 | 2/2014 | Turner et al. |
| 9,194,838 B2 | 11/2015 | Taniguchi et al. |
| 9,506,894 B2 | 11/2016 | Kawai et al. |
| 9,535,033 B2 | 1/2017 | Tomoji et al. |
| 9,644,236 B2 | 5/2017 | Kawai et al. |
| 10,202,644 B2 | 2/2019 | Taniguchi et al. |
| 2001/0046681 A1 | 11/2001 | Senapathy |
| 2002/0046953 A1 | 4/2002 | Lee et al. |
| 2002/0081744 A1 | 6/2002 | Chan et al. |
| 2002/0168671 A1 | 11/2002 | Burns et al. |
| 2002/0168810 A1 | 11/2002 | Jackson |
| 2003/0052006 A1 | 3/2003 | Noca et al. |
| 2003/0075445 A1 | 4/2003 | Woudenberg et al. |
| 2003/0085719 A1 | 5/2003 | Yoon et al. |
| 2003/0089606 A1 | 5/2003 | Parce et al. |
| 2003/0104428 A1 | 6/2003 | Branton et al. |
| 2003/0141189 A1 | 7/2003 | Lee et al. |
| 2003/0207326 A1 | 11/2003 | Su et al. |
| 2004/0124084 A1 | 7/2004 | Lee et al. |
| 2004/0144658 A1 | 7/2004 | Flory |
| 2004/0161708 A1 | 8/2004 | Nagase et al. |
| 2005/0048513 A1 | 3/2005 | Harwit et al. |
| 2005/0051768 A1 | 3/2005 | Kim et al. |
| 2005/0061669 A1 | 3/2005 | Woudenberg et al. |
| 2005/0084865 A1 | 4/2005 | Yu et al. |
| 2005/0112860 A1 | 5/2005 | Park et al. |
| 2005/0127035 A1 | 6/2005 | Ling |
| 2005/0136419 A1 | 6/2005 | Lee |
| 2005/0202444 A1 | 9/2005 | Zhu |
| 2005/0202446 A1 | 9/2005 | Yang et al. |
| 2005/0227239 A1 | 10/2005 | Joyce |
| 2006/0011480 A1 | 1/2006 | Sano et al. |
| 2006/0057585 A1 | 3/2006 | McAllister |
| 2006/0071209 A1 | 4/2006 | Flory et al. |
| 2006/0154399 A1 | 7/2006 | Sauer et al. |
| 2006/0154400 A1 | 7/2006 | Choi et al. |
| 2006/0210995 A1 | 9/2006 | Joyce |
| 2006/0275911 A1 | 12/2006 | Wang et al. |
| 2007/0029911 A1* | 2/2007 | Hudspeth ............... H01J 1/304 313/309 |
| 2007/0042366 A1 | 2/2007 | Ling |
| 2007/0171714 A1 | 7/2007 | Wu et al. |
| 2007/0183198 A1 | 8/2007 | Otsuka et al. |
| 2008/0077607 A1 | 3/2008 | Gatawood et al. |
| 2008/0119366 A1 | 5/2008 | Sauer et al. |
| 2008/0171316 A1 | 7/2008 | Golovchenko et al. |
| 2008/0215252 A1 | 9/2008 | Kawai et al. |
| 2008/0248561 A1 | 10/2008 | Golovchenko et al. |
| 2009/0023146 A1 | 1/2009 | Harnack et al. |
| 2009/0155917 A1 | 6/2009 | Umezawa et al. |
| 2009/0215156 A1 | 8/2009 | Chung et al. |
| 2009/0229854 A1 | 9/2009 | Fredenberg et al. |
| 2009/0242429 A1 | 10/2009 | Sitdikov et al. |
| 2009/0283412 A1 | 11/2009 | Sansinena et al. |
| 2009/0286936 A1 | 11/2009 | Ogata et al. |
| 2009/0305273 A1 | 12/2009 | Cao et al. |
| 2010/0025249 A1 | 2/2010 | Polonsky et al. |
| 2010/0066348 A1 | 3/2010 | Merz et al. |
| 2010/0084276 A1 | 4/2010 | Lindsay |
| 2010/0184062 A1 | 7/2010 | Steinmuller-Nethl et al. |
| 2010/0188109 A1 | 7/2010 | Edel et al. |
| 2010/0243449 A1 | 9/2010 | Oliver |
| 2010/0267158 A1 | 10/2010 | Chou et al. |
| 2010/0292101 A1 | 11/2010 | So |
| 2010/0331194 A1 | 12/2010 | Turner et al. |
| 2011/0056845 A1 | 3/2011 | Stellacci et al. |
| 2011/0171634 A1 | 7/2011 | Xiao et al. |
| 2011/0179852 A1 | 7/2011 | Polonsky et al. |
| 2011/0193183 A1 | 8/2011 | Agarwal et al. |
| 2011/0236984 A1 | 9/2011 | Sun et al. |
| 2011/0250464 A1* | 10/2011 | Wilson ............... B22F 1/0018 428/570 |
| 2011/0287956 A1 | 11/2011 | Iqbal et al. |
| 2012/0041727 A1 | 2/2012 | Mishra et al. |
| 2012/0097539 A1 | 4/2012 | Qian et al. |
| 2012/0132886 A1 | 5/2012 | Peng et al. |
| 2012/0184047 A1 | 7/2012 | Jonsson et al. |
| 2012/0193237 A1 | 8/2012 | Afzali-ardakani et al. |
| 2012/0199485 A1 | 8/2012 | Sauer et al. |
| 2012/0254715 A1 | 10/2012 | Schwartz |
| 2012/0298511 A1 | 11/2012 | Yamamoto |
| 2012/0322055 A1 | 12/2012 | Royyuru |
| 2013/0001082 A1 | 1/2013 | Afzali-ardakani et al. |
| 2013/0092547 A1 | 4/2013 | Li et al. |
| 2013/0157271 A1 | 6/2013 | Coursey et al. |
| 2013/0186758 A1 | 7/2013 | Saha et al. |
| 2013/0264207 A1 | 10/2013 | Ju et al. |
| 2013/0334047 A1 | 12/2013 | Jeong et al. |
| 2014/0001055 A1 | 1/2014 | Elibol et al. |
| 2014/0008225 A1 | 1/2014 | Jeon et al. |
| 2014/0031995 A1 | 1/2014 | Kawai et al. |
| 2014/0055150 A1 | 2/2014 | Kawai et al. |
| 2014/0103945 A1 | 4/2014 | Eid et al. |
| 2014/0183040 A1 | 7/2014 | Kawai et al. |
| 2014/0202857 A1 | 7/2014 | Valbusa et al. |
| 2014/0273186 A1 | 9/2014 | Oxenrider |
| 2014/0300339 A1 | 10/2014 | Taniguchi et al. |
| 2014/0302675 A1 | 10/2014 | Astier et al. |
| 2014/0364324 A1 | 12/2014 | Turner et al. |
| 2014/0374695 A1* | 12/2014 | Astier ............... G01N 33/48721 257/9 |
| 2015/0107996 A1 | 4/2015 | Chen |
| 2015/0111759 A1 | 4/2015 | Ju et al. |
| 2015/0132756 A1 | 5/2015 | Peter et al. |
| 2015/0310228 A1 | 10/2015 | Benz et al. |
| 2015/0323490 A1 | 11/2015 | Luan et al. |
| 2016/0048690 A1 | 2/2016 | Tanishima et al. |
| 2016/0049327 A1* | 2/2016 | Singh ............... H01L 21/76814 438/666 |
| 2016/0138101 A1 | 5/2016 | Taniguchi et al. |
| 2016/0245789 A1 | 8/2016 | Ikeda et al. |
| 2016/0245790 A1 | 8/2016 | Kawai et al. |
| 2016/0319342 A1 | 11/2016 | Kawai et al. |
| 2016/0377591 A1 | 12/2016 | Kawai et al. |
| 2017/0131237 A1 | 5/2017 | Ikeda |
| 2017/0144158 A1 | 5/2017 | Taniguchi |
| 2017/0146510 A1 | 5/2017 | Ikeda et al. |
| 2017/0146511 A1 | 5/2017 | Taniguchi et al. |
| 2018/0023132 A1 | 1/2018 | Kawai et al. |

FOREIGN PATENT DOCUMENTS

| | | |
|---|---|---|
| CN | 102180440 A | 9/2011 |
| CN | 102914395 A | 2/2013 |
| EP | 1419112 A1 | 5/2004 |
| EP | 2573554 A1 | 3/2013 |
| JP | 62-194673 A | 8/1987 |
| JP | S6437640 A | 2/1989 |
| JP | 04-302151 A | 10/1992 |
| JP | H04302151 A | 10/1992 |
| JP | H 0774337 A | 3/1995 |
| JP | H10283230 A | 10/1998 |
| JP | 2003507026 A | 2/2003 |
| JP | 2003/090815 A | 3/2003 |
| JP | 2003/332555 A | 11/2003 |
| JP | 2003/533676 A | 11/2003 |
| JP | 2004/233356 A | 8/2004 |
| JP | 2004247203 A | 9/2004 |
| JP | 2004303162 A | 10/2004 |
| JP | 2005501234 A | 1/2005 |
| JP | 2005/257687 A | 9/2005 |
| JP | 2006/078491 A | 3/2006 |
| JP | 2006/526777 A | 11/2006 |
| JP | 2007/272212 A | 10/2007 |
| JP | 2008/032529 A | 2/2008 |
| JP | 2008146538 A | 6/2008 |
| JP | 4128573 B2 | 7/2008 |
| JP | 2008/186975 A | 8/2008 |
| JP | 2008/536124 A | 9/2008 |
| JP | 2009/527817 A | 7/2009 |
| JP | 4289938 B2 | 7/2009 |
| JP | 2009210272 A | 9/2009 |
| JP | 2009/272432 A | 11/2009 |

(56) References Cited

FOREIGN PATENT DOCUMENTS

| | | |
|---|---|---|
| JP | 2010/513853 A | 4/2010 |
| JP | 2010510476 A | 4/2010 |
| JP | 2010/227735 A | 10/2010 |
| JP | 2011/500025 A | 1/2011 |
| JP | 2011/054631 A | 3/2011 |
| JP | 2011/516050 A | 5/2011 |
| JP | 4719906 B2 | 7/2011 |
| JP | 2011/163934 A | 8/2011 |
| JP | 2011/211905 A | 10/2011 |
| JP | 2012/110258 A | 6/2012 |
| JP | 2012118709 A | 6/2012 |
| JP | 2013/036865 A | 2/2013 |
| JP | 2013090576 A | 5/2013 |
| JP | 2013518283 A | 5/2013 |
| JP | 2013519074 A | 5/2013 |
| JP | 2013215725 A | 10/2013 |
| JP | 2014/074599 A | 4/2014 |
| JP | 2014173936 A | 9/2014 |
| JP | 2015/059824 A | 3/2015 |
| JP | 2015/077652 A | 4/2015 |
| KR | 1020140031559 | 3/2014 |
| TW | 200619614 A | 6/2006 |
| TW | 200637916 A | 11/2006 |
| TW | 200907068 A | 2/2009 |
| TW | 201013179 A | 4/2010 |
| TW | 201100796 A | 1/2011 |
| WO | WO 01/13088 A1 | 2/2001 |
| WO | WO 01/81896 A1 | 11/2001 |
| WO | WO 01/81908 A1 | 11/2001 |
| WO | WO 03/018484 A1 | 3/2003 |
| WO | WO-03042396 A2 | 5/2003 |
| WO | WO 2003/106693 A2 | 12/2003 |
| WO | WO 2007/013370 A1 | 2/2007 |
| WO | WO 2008/079169 A2 | 7/2008 |
| WO | WO-2008071982 A3 | 7/2008 |
| WO | WO 2009/045472 A1 | 4/2009 |
| WO | WO 2009/093019 A2 | 7/2009 |
| WO | WO 2009/120642 A1 | 10/2009 |
| WO | WO 2009/149362 A2 | 12/2009 |
| WO | WO-2010111605 A2 | 9/2010 |
| WO | WO 2010/116595 A1 | 10/2010 |
| WO | WO-2010111605 A3 | 11/2010 |
| WO | WO 2011/082419 A1 | 7/2011 |
| WO | WO 2011/097171 A1 | 8/2011 |
| WO | WO 2011/108540 A1 | 9/2011 |
| WO | WO-2012009578 A2 | 1/2012 |
| WO | WO-2012009578 A3 | 4/2012 |
| WO | WO 2012/164679 A1 | 12/2012 |
| WO | WO 2012/170560 A2 | 12/2012 |
| WO | WO-2013016486 A1 | 1/2013 |
| WO | WO 2013/076943 A1 | 5/2013 |
| WO | WO-2013066456 A2 | 5/2013 |
| WO | WO-2013074546 A1 | 5/2013 |
| WO | WO 2013/100949 A1 | 7/2013 |
| WO | WO-2013066456 A3 | 7/2013 |
| WO | WO 2013/116509 A1 | 8/2013 |
| WO | WO-2013115185 A1 | 8/2013 |
| WO | WO 2013/147208 A1 | 10/2013 |
| WO | WO-2014027580 A1 | 2/2014 |
| WO | WO-2015028885 A2 | 3/2015 |
| WO | WO-2015028886 A2 | 3/2015 |
| WO | WO-2015042200 A1 | 3/2015 |
| WO | WO-2015028885 A3 | 4/2015 |
| WO | WO-2015057870 A1 | 4/2015 |
| WO | WO-2015028886 A3 | 5/2015 |
| WO | WO-2015111760 A1 | 7/2015 |
| WO | WO-2015125920 A1 | 8/2015 |
| WO | WO-2015167019 A1 | 11/2015 |
| WO | WO-2015170782 A1 | 11/2015 |
| WO | WO-2015170783 A1 | 11/2015 |
| WO | WO-2015170784 A1 | 11/2015 |
| WO | WO-2016206593 A1 | 12/2016 |
| WO | WO-2017061129 A1 | 4/2017 |
| WO | WO-2017179581 A1 | 10/2017 |
| WO | WO-2017189930 A1 | 11/2017 |
| WO | WO-2018025887 A1 | 2/2018 |
| WO | WO-2019065904 A1 | 4/2019 |

OTHER PUBLICATIONS

Cheng, et al. Development of an electrochemical membrane-based nanobiosensor for ultrasensitive detection of dengue virus. Anal Chim Acta. May 6, 2012;725:74-80. doi: 10.1016/j.aca.2012.03.017. Epub Mar. 17, 2012.

European search report and opinion dated Apr. 8, 2016 for EP Application No. 13879507.5.

Gonzalez, et al. Mass transport effect of mesoscopic domains in the amperometric response of an electroactive species: Modeling for its applications in biomolecule detection. Sensors and Actuators B: Chemical 144.2 (2010): 349-353.

He, et al. Gate manipulation of DNA capture into nanopores. ACS Nano. Oct. 25, 2011;5(10):8391-7. doi: 10.1021/nn203186c. Epub Sep. 26, 2011.

He, et al. Thermophoretic manipulation of DNA translocation through nanopores. ACS Nano. Jan. 22, 2013;7(1):538-46. doi: 10.1021/nn304914j. Epub Dec. 10, 2012.

Lee, et al. Surface charge study on pollen with a simple microelectrophoresis instrumentation setup. Biomedical Engineering and Sciences (IECBES), 2010 IEEE EMBS Conference on. Kuala Lumpur, Malaysia, Nov. 30-Oct. 2, 2010, pp. 364-368.

Office action dated May 25, 2016 for U.S. Appl. No. 14/421,809.

Office action dated Jun. 23, 2016 for U.S. Appl. No. 14/111,352.

Smith, et al. Electrophoretic distributions of human peripheral blood mononuclear white cells from normal subjects and from patients with acute lymphocytic leukemia. Proc Natl Acad Sci U S A. Jul. 1976;73(7):2388-91.

Tsutsui, et al. Transverse electric field dragging of DNA in a nanochannel. Sci Rep. 2012;2:394. doi: 10.1038/srep00394. Epub May 3, 2012.

Woolley, et al. Capillary electrophoresis chips with integrated electrochemical detection. Analytical Chemistry 70.4 (1998): 684-688.

U.S. Appl. No. 15/048,810, filed Feb. 19, 2016, Ikeda et al.
U.S. Appl. No. 15/048,889, filed Feb. 19, 2016, Kawai et al.
U.S. Appl. No. 15/061,871, filed Mar. 4, 2016, Kawai et al.
U.S. Appl. No. 15/098,147, filed Apr. 13, 2016, Ikeda et al.

He, et al. Controlling DNA translocation through gate modulation of nanopore wall surface charges. ACS Nano. Jul. 26, 2011;5(7):5509-18. doi: 10.1021/nn201883b. Epub Jun. 17, 2011.

Nam, et al. Ionic field effect transistors with sub-10 nm multiple nanopores. Nano Lett. May 2009;9(5):2044-8. doi: 10.1021/nl900309s.

Office action dated Feb. 5, 2016 for U.S. Appl. No. 14/112,189.
Office action dated Feb. 19, 2016 for U.S. Appl. No. 13/975,610.
U.S. Appl. No. 14/421,809, filed Feb. 13, 2015, Kawai.

Bagci, et al. Recognizing nucleotides by cross-tunneling currents for DNA sequencing. Physical Review E, vol. 84, Issue No. 1, Article No. 011917 (internal pp. 1-4) (2011).

Branton, et al. The potential and challenges of nanopore sequencing. Nature Biotechnology, vol. 26, No. 10, Oct. 2008, pp. 1146-1153.

Brown, et al. Nucleotide-Surface Interactions in DNA-Modified Au-Nanoparticle Conjugates: Sequence Effects on Reactivity and Hybridization. J. Phys. Chem. C, 2008, 112 (20), pp. 7517-7521.

Chang, et al. Tunnelling readout of hydrogen-bonding-based recognition. Nature Nantechnology, vol. 4, May 2009, pp. 297-301.

Clarke, et al. Continuous base identification for single-molecule nanopore DNA sequencing. Nat Nanotechnol. Apr. 2009;4(4):265-70. doi: 10.1038/nnano.2009.12. Epub Feb. 22, 2009.

Dekker, et al. Solid-state nanopores. Nature Nanotechnology, vol. 2, Apr. 2007, pp. 209-215.

Fischbein, et al. Sub-10 nm Device Fabrication in a Transmission Electron Microscope. American Chemical Society, Nano Letters, 2007, vol. 7, No. 5, pp. 1329-1337.

Fologea, et al. Detecting Single Stranded DNA with a Solid State Nanopore. American Chemical Society, Nano Letters, 2005, vol. 5, No. 10, pp. 1905-1909.

(56) References Cited

OTHER PUBLICATIONS

Furuhashi, et al. High speed DNA denaturation using microheating devices. Appl. Phys. Lett., Jul. 11, 2013, 103, pp. 023112.
He, et al. Identification of DNA Basepairing via Tunnel-Current Decay. American Chemical Society, Nano Letters, 2007, vol. 7, No. 12, pp. 3854-3858.
International Preliminary Report on Patentability dated Jun. 25, 2013 for PCT Application No. JP2013/059645.
International search report and written opinion dated Jan. 26, 2015 for PCT Application No. US2014/060742.
International search report and written opinion dated Oct. 29, 2013 for PCT Application No. JP2013/071059.
International search report and written opinion dated Dec. 19, 2014 for PCT Application No. US2014/056173.
International search report dated Feb. 17, 2015 for PCT Application No. IB2014/002143.
International search report dated Feb. 24, 2015 for PCT Application No. IB2014/002128.
International search report dated Jun. 25, 2013 for PCT Application No. JP2013/059645.
Kaji, et al. Separation of long DNA molecules by quartz nanopillar chips under a direct current electric field. Anal. Chem., Jan. 1, 2004, 76(1): pp. 15-22.
Keyser, et al. Direct force measurements on DNA in a solid-state nanopore. Nature Physics, vol. 2, Jul. 2006, pp. 473-477.
Lagerqvist, et al. "Fast DNA Sequencing via Transverse Electronic Transport", American Chemical Society, Nano Letters, 2006, vol. 6, No. 4, pp. 779-782.
Lagerqvist, et al. Influence of the Environment and Probes on Rapid DNA Sequencing via Transverse Electronic Transport. Biophysical Journel, vol. 93, Oct. 2007, pp. 23842390.
Li, et al. Ion-beam sculpting at nanometer length scales. Nature, vol. 412, Jul. 2001, pp. 166-169.
Liang, et al. Nanogap Detector Inside nanofluidic Channel for Fast Real-Time Label-Free DNA Analysis. American Chemical Society, Nano Letters 2008, vol. 8, No. 5, pp. 1472-1476.
Maleki, et al. A nanofluidic channel with embedded transverse nanoelectrodes. Nanotechnology, 20, (2009) 105302, pp. 1-6.
Nadasan, et al. Design and fabrication of the microchannels for microfluidics applications. U.P.B. Sci. Bull., Series C, 2009, 71(4): pp. 125-134.
Office action dated Apr. 17, 2015 for U.S. Appl. No. 13/992,328.
Oshiro, et al. Detection of post-translational modifications in single peptides using electron tunnelling currents. Nature Nanotechnology, vol. 9, pp. 835-840 (e-pub. Sep. 14, 2014).
Oshiro, et al. Single-molecule electrical random resequencing of DNA and RNA. Scientific Reports, vol. 2, Article No. 501 (internal pp. 1-7) (e-pub. Jul. 10, 2012) See abstract: p. 2; figures 1-4; and tables 1-3.
Pedone, et al. Data Analysis of Translocation Events in Nanopore Experiments. American Chemical Society, Anal. Chem. 2009, 81, pp. 9689-9694.
Peng, et al. Reverse DNA translocation through a solid-state nanopore by magnetic tweezers. Nanotechnology. May 6, 2009;20(18):185101. doi: 10.1088/0957-4484/20/18/185101. Epub Apr. 14, 2009.
Ruitenbeek, et al. Adjustable nanofabricated atomic size contacts. Rev. Sci. Instrum. 67, 108 (1996).
Simmons, et al. Generalized Formula for the Electric tunnele Effect between Similar Electrodes Separated by a Thin Insulating Film. J. Appl. Phys. 34, 1793 (1963).
Stijin Van Dorp, et al. Origin of the electrophoretic force on DNA in solid-state nanopores. Nature Physics, vol. 5, May 2009, pp. 347-351.
Stoddart, et al. Single-nucleotide discrimination in immobilized DNA oligonucleotides with a biological nanopore. PNAS, May 12, 2009, vol. 106, No. 19, pp. 7702-7707.
Storm, et al. Fabrication of solid-state nanopores with single-nanometere precision. Nature Materials, vol. 2, Aug. 2003, pp. 537-540.
Taniguchi, et al. Denryu de Ichi Enki Bunshi o Shikibetsu suru. Chemistry, 2011, vol. 66, No. 8, pp. 42-46.
Taniguchi, et al. Development of Single-Molecule Bio-Nanodevies for Medical Applications. The Imaging Society of Japan, Feb. 10, 2013, vol. 52, No. 1, pp. 51-60.
Taniguchi, M. Ichibunshi Kaiseki Gijutsu ni yoru Jijisedai DNA Sequencer no Kaihatsu. Dai 69 Kai Hyomen Kagaku Kenkyukai Yoshishu. Mar. 9, 2011, pp. 23-26.
Trepagnier, et al. Controlling DNA Capture and Progagation through Artificial Nanopores. American Chemical Society, Nano Letters, 2007, vol. 7, No. 9, pp. 2824-2830.
Tsutsui, et al. Fabrication of 0.5 nm electrode gaps using self-breaking technique. Applied Physics Letters 93, 163115 (2008); DOI: 10.1063/1.3006063.
Tsutsui, et al. Formation and self-breaking mechanism of stable atom-sized junctions. Nano Lett. Jan. 2008;8(1):345-9. Epub Dec. 21, 2007.
Tsutsui, et al. Identifying single nucleotides by tunnelling current. Nature Nanotechnology, Letters, Published Online: Mar. 21, 2010; DOI: 10.1038/NNANO.2010.42, pp. 1-5.
Tsutsui, et al. Transverse Field Effects on DNA-Sized Particle Dynamics. American Chemical Society, Nano Letters, 2009, vol. 9, No. 4, pp. 1659-1662.
Wang, et al. Mechanism of electron conduction in self-assembled alkanethiol monolayer devices. Phys. Rev. B 68, 035416— Published Jul. 17, 2003.
Yen, et al. Gate effects on DNA translocation through silicon dioxide nanopore. Rev Sci Instrum. Mar. 2012;83(3):034301. doi: 10.1063/1.3692746.
Zhou, et al. Microfabrication of a mechanically controllable break junction in silicon. Appl. Phys. Lett. 67, 1160 (1995).
Zwolak, et al. Colloquium: Physical approaches to DNA sequencing and detection. Reviews of Modern Physics, vol. 80, Jan.-Mar. 2008, pp. 141-165.
Zwolak, et al. Electronic Signature of DNA Nucleotides via Transverse Transport. American Chemical Society, Nano Letters, 2005, vol. 5, No. 3, pp. 421-424.
Notice of allowance dated Jul. 21, 2016 for U.S. Appl. No. 13/975,610.
Office action dated Aug. 1, 2016 for U.S. Appl. No. 14/112,189.
Qiu, et al. Detecting ssDNA at single-nucleotide resolution by sub-2-nanometer pore in monatomic graphene: A molecular dynamics study. Applied Physics Letters 100.8 (2012): 083106. 4 pages.
Zhao, et al. Single-strand DNA molecule translocation through nanoelectrode gaps. Nanotechnology. Oct. 24, 2007;18(42):424018. doi: 10.1088/0957-4484/18/42/424018. Epub Sep. 19, 2007. 7 pages.
Huang, et al. Identifying single bases in a DNA oligomer with electron tunnelling. Nat Nanotechnol. Dec. 2010;5(12):868-73. doi: 10.1038/nnano.2010.213. Epub Nov. 14, 2010.
Notice of allowance dated Jul. 17, 2015 for U.S. Appl. No. 13/992,328.
Office action dated Sep. 1, 2015 for U.S. Appl. No. 14/112,189.
Notice of allowance dated Oct. 8, 2015 for U.S. Appl. No. 13/992,328.
U.S. Appl. No. 14/883,494, filed Oct. 14, 2015, Taniguchi et al.
Troisi, et al. Molecular signatures in the transport properties of molecular wire junctions: what makes a junction "molecular"? Small. Feb. 2006;2(2):172-81.
Co-pending U.S. Appl. No. 16/266,363, filed Feb. 4, 2019.
Office action dated Sep. 9, 2016 for U.S. Appl. No. 15/061,871.
Co-pending U.S. Appl. No. 15/937,327, filed Mar. 27, 2018.
Suga et al. Influence of electrode size on resistance switching effect in nanogap junctions, Applied Physics Letter, 2010, 97(7):73118, 4 pages. Epub Aug. 20, 2010.
Notice of allowance dated Sep. 15, 2016 for U.S. Appl. No. 14/421,809.
Office action dated Oct. 6, 2016 for U.S. Appl. No. 14/883,494.
Anima et al. Fabrications of insulator-protected nanometer-sized electrode gaps. Journal of Applied Physics 115:114310 (2014). 6 pages. doi: 10.1063/1.4869135.
Co-pending U.S. Appl. No. 16/156,755, filed Oct. 10, 2018.
Co-pending U.S. Appl. No. 16/169,756, filed Oct. 24, 2018.
Co-pending U.S. Appl. No. 16/178,924, filed Nov. 2, 2018.
Co-pending U.S. Appl. No. 16/234,908, filed Dec. 28, 2018.

(56) References Cited

OTHER PUBLICATIONS

Ohshiro et al. Supplementary Information for Single-Molecule Electrical Random Resequencing of DNA and RNA. Scientific Reports 2, Article No. 501 (Jul. 10, 2012). 23 pages. doi:10.1038/srep00501.

Tsutsui et al. Electrical Detection of Single-Methylcytosines in a DNA Oligomer. J Am Chem Soc 133(23): 9124-9128 (May 11, 2011). DOI: 10.1021/ja203839e.

Tsutsui et al. Supplementary Information for Identifying Single Nucleotides by Tunneling Current. Nature Nanotechnology 5:286-290 (Mar. 21, 2010). doi: 10.1038/NNANO.2010.42.

Tsutsui et al. Supporting Information for Electrical Detection of Single-Methylcytosines in a DNA Oligomer. J Am Chem Soc 133(23): 9124-9128 (May 11, 2011). DOI: 10.1021/ja203839e.

Co-pending U.S. Appl. No. 15/242,221, filed Aug. 19, 2016.
Co-pending U.S. Appl. No. 15/336,515, filed Oct. 27, 2016.
Co-pending U.S. Appl. No. 15/340,584, filed Nov. 1, 2016.
Co-pending U.S. Appl. No. 15/344,184, filed Nov. 4, 2016.
Co-pending U.S. Appl. No. 15/344,199, filed Nov. 4, 2016.
Co-pending U.S. Appl. No. 15/448,317, filed Mar. 2, 2017.

Chen, et al., A novel nanofabrication technique for the array of Nanogap electrodes, Japanese Journal of Applied Physics, Japan Society of Applied physics, JP, 2006, 45(6):5531-5534.

El-Ali, et al., Simulation and experimental validation of a SU-8 based PCR themorcycler chp with integrated heaters and temperature sensor, Sensors and Actuators A, 110, 2004, pp. 3-10.

Hashioka, et al, Metal nanogap devices fabricated by conventional photolithography and their application to deoxyribose nucleic acid analysis, Journal of Vacuum Science & Technology B: microelectronics; Materials, Processing and Phenomena, 2003, 21(6):2937-40.

Tsutsui, et al., Formation and self-breaking mechanism of stable atom-sized junctions, Nano Letters, 2008, 8(1):345-349.

Axopatch 2008 Patch Clamp: Theory and Operation, Axon Instruments, Inc., Mar. 1999.

Chen, et al., Probing Single DNA Molecule Transport Using Fabricated Nanopores, Nano Letters, 2004, 4(11):2293-2298.

International Search Report and Written Opinion dated Dec. 6, 2016 for International Application No. PCT/JP2016/004531.

Notice of Allowance dated Dec. 6, 2016 for U.S. Appl. No. 15/061,871.

Office Action dated Jan. 27, 2017 for U.S. Appl. No. 14/111,352.

Rothberg, J.M. et al., An integrated semiconductor device enabling non-optical genome sequencing, Nature. 2011. 475(7356). pp. 348-352.

U.S. Appl. No. 15/217,821, filed Jul. 22, 2016, Kawai et al.

Gierhart, et al. Nanopore with transverse nanoelectrodes for electrical characterization and sequencing of DNA. Sens Actuators B Chem. Jun. 16, 2008;132(2):593-600.

International search report and written opinion dated May 19, 2015 for PCT/JP2015/054796.

International search report and written opinion dated Jun. 24, 2015 for PCT/JP2015/052601.

International search report and written opinion dated Aug. 11, 2015 for PCT/JP2015/063403.

International search report and written opinion dated Aug. 18, 2015 for PCT/JP2015/063964.

International search report and written opinion dated Aug. 18, 2015 for PCT/JP2015/063965.

International search report and written opinion dated Aug. 18, 2015 for PCT/JP2015/063963.

Ivanov, et al. DNA tunneling detector embedded in a nanopore. Nano Lett. Jan. 12, 2011;11(1):279-85. doi: 10.1021/nl103873a. Epub Dec. 6, 2010.

Lesser-Rojas, et al. Tandem array of nanoelectronic readers embedded coplanar to a fluidic nanochannel for correlated single biopolymer analysis. Biomicrofluidics. Jan. 10, 2014;8(1):016501. doi: 10.1063/1.4861435. eCollection 2014. With Supplementary Materials.

Ohshiro, et al. Single-molecule electrical random resequencing of DNA and RNA. Scientific Reports 2, Article No. 501 (Jul. 10, 2012) doi:10.1038/srep00501.

Venkatesan, et al. Nanopore sensors for nucleic acid analysis. Nat Nanotechnol. Sep. 18, 2011;6(10):615-24. doi: 10.1038/nnano.2011.129.

Feng, et al. "Nanopore-based Fourth-generation DNA Sequencing Technology" Genomics, Proteomics & Bioinformatics. 2015; 13(1):4-16, p. 5, co12, para 3.

Fuller, et al. "Real-time single-molecule electronic DNA sequencing by synthesis using polymer-tagged nucleotides on a nanopore array" PNAS, Mar. 18, 2016 (Mar. 18, 2016); 113(19):5233-5238 (doi: 10.1073/pnas.1601782113) p. 5234, col. 1, para 1-3; p. 5235, col. 1, para 1; p. 5236, col. 1, para 1; Fig. 2.

Schreiber, et al. "Error rates for nanopore discrimination among cytosine, methylcytosine, and hydroxymethylcytosine along individual DNA strands" PNAS, 2013; 11 0(47): 18910-18915, p. 18910, col. 2, para 3.

Armbrust et al. Clearing the clouds away from the true potential and obstacles posed by this computing capability. Communications of the ACM 53(4):50-58 (Apr. 2010).

Furuhashi et al. Denaturation of DNAs in a nanofluidic channel by micro-heating method. The 74th Annual Meeting of the Japan Society of Applied Physics Lecture Papers p. 12-295 (Aug. 2013).

Furuhashi et al. Denature of double-stranded DNAs by a micro-heating method. Proceedings of the 60th Spring Science Lecture Meeting of the Japan Society of Applied Physics, p. 12-356, (Mar. 2013).

Garcia-Lekue et al. Plane-wave-based electron tunneling through Au nanojunctions: Numerical calculations. Physical Review B 82:035410 (2010). 9 pages.

Healy et al. Fabrication and characterization of nanopores with insulated transverse nanoelectrodes for DNA sensing in salt solution. Electrophoresis 33(23) (Dec. 2012). doi: 10.1002/elps.201200350. 15 pages.

* cited by examiner

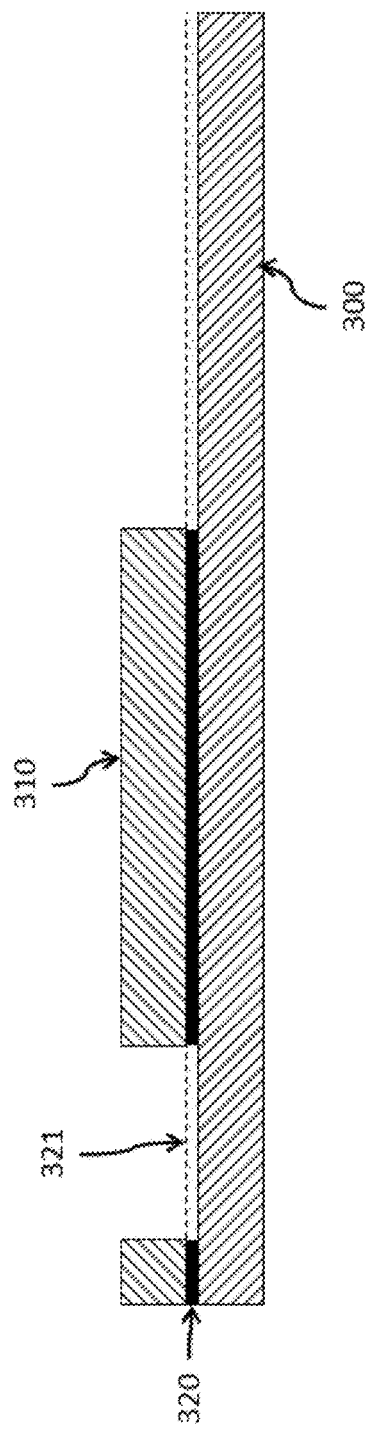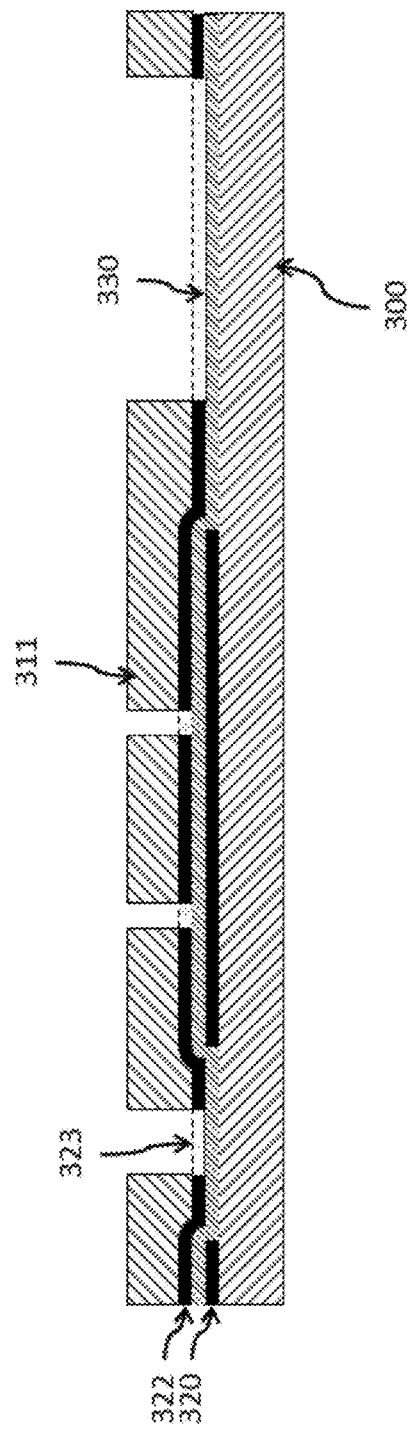
FIG. 3A
FIG. 3B

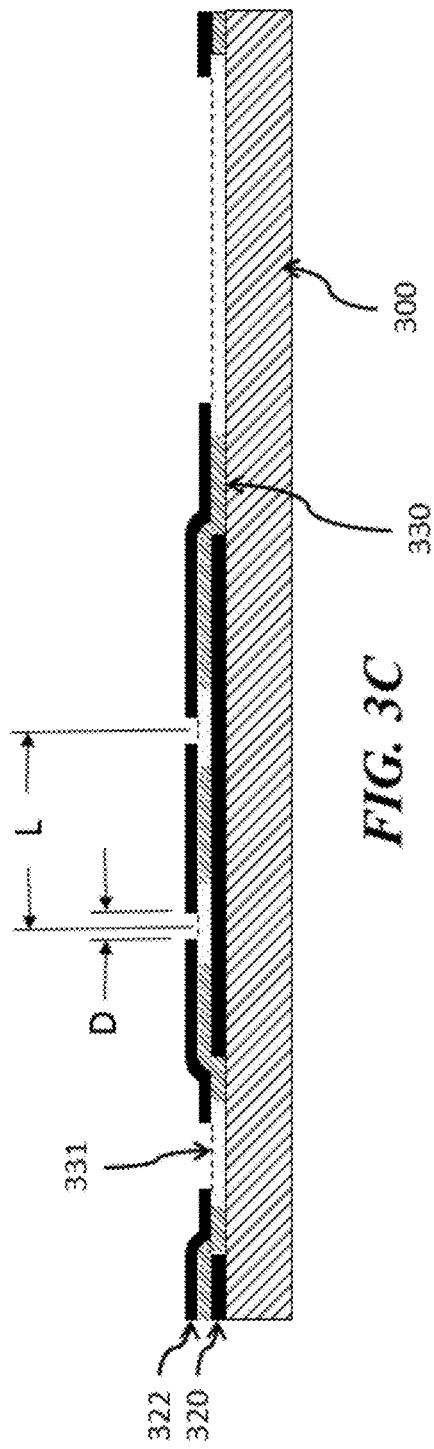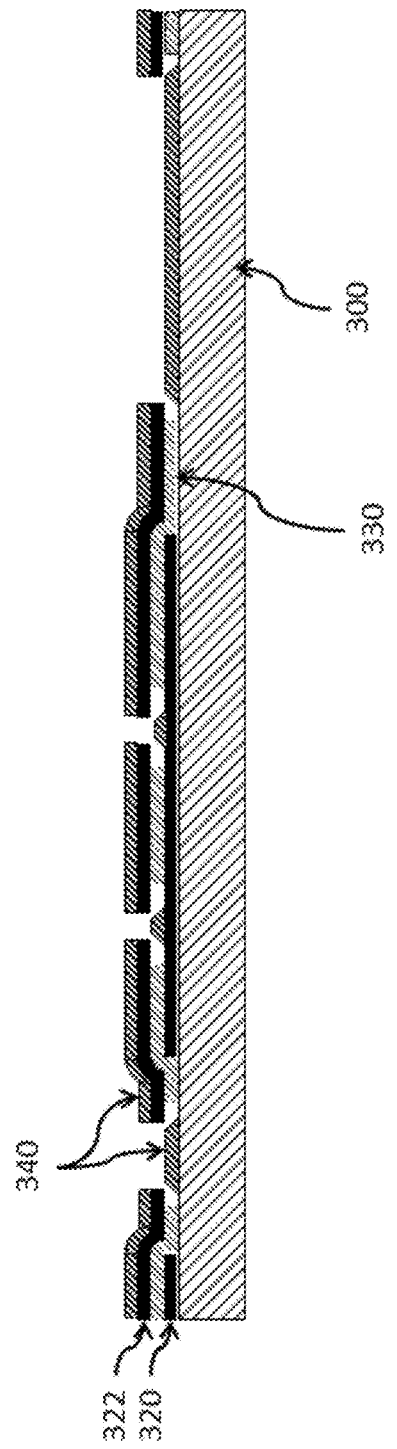
FIG. 3C
FIG. 3D

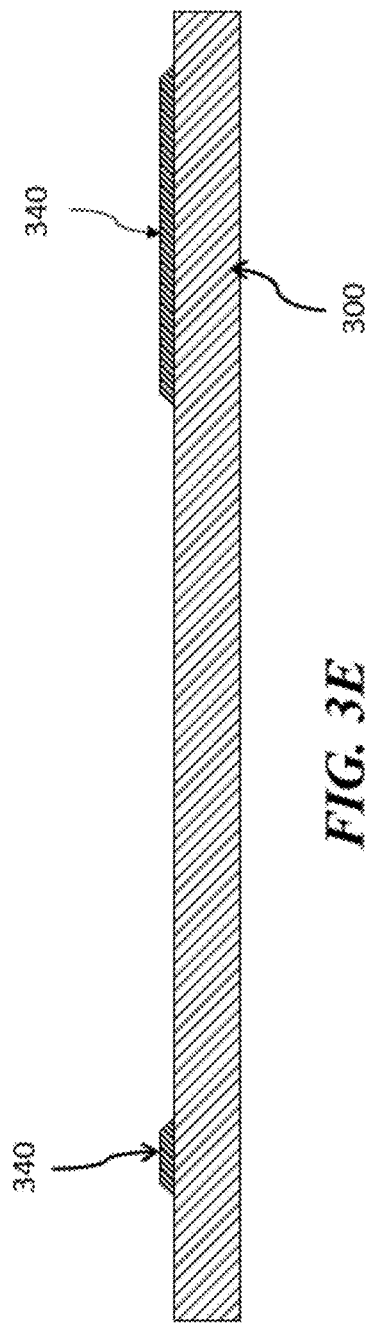

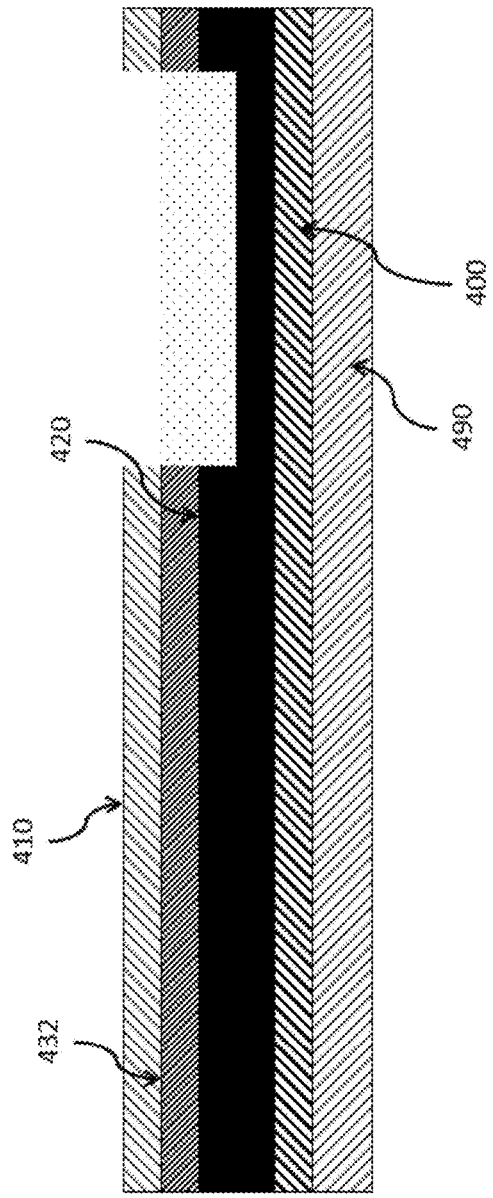
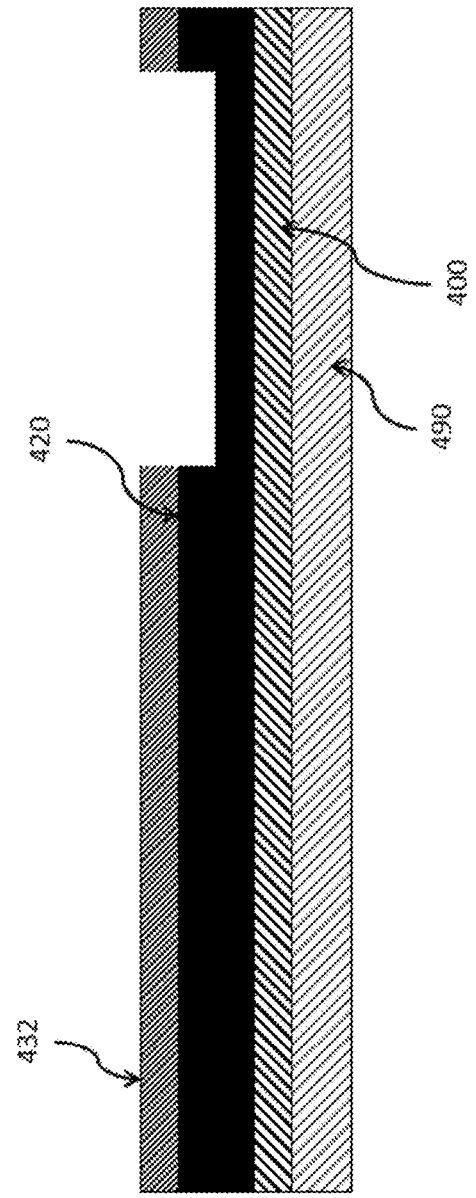
FIG. 4B
FIG. 4C

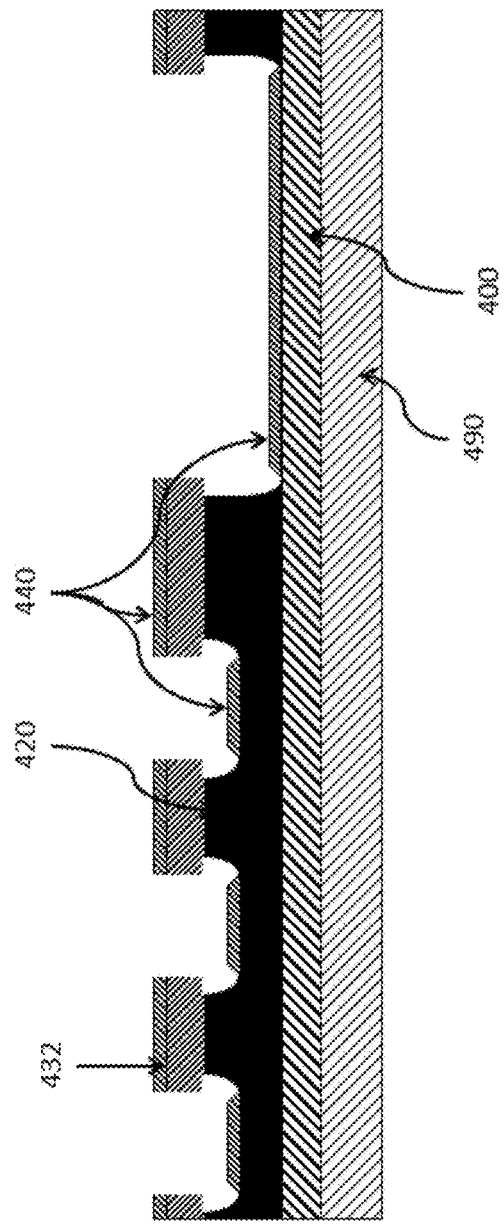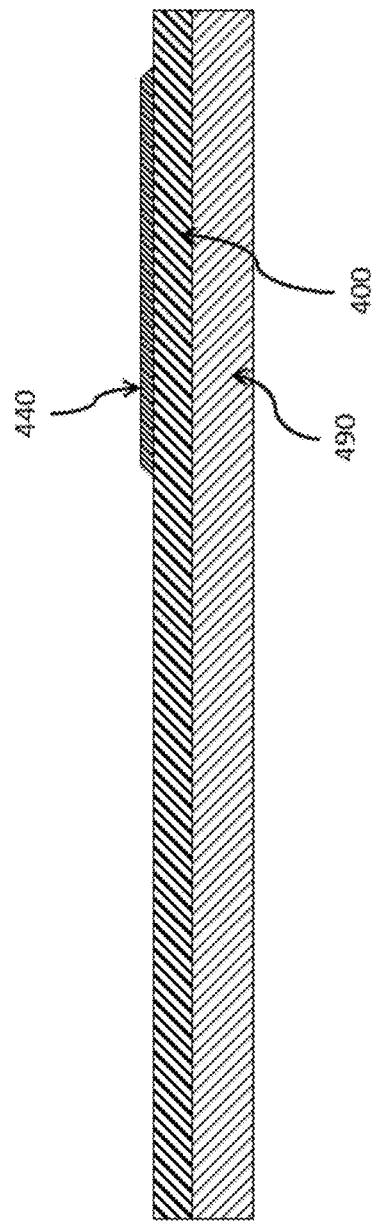
FIG. 4F
FIG. 4G

METHODS FOR FORMING NANO-GAP ELECTRODES FOR USE IN NANOSENSORS

CROSS-REFERENCE

This application claims priority to U.S. Provisional Patent Application No. 61/995,600, filed Apr. 15, 2014, which is entirely incorporated herein by reference.

BACKGROUND

Nanopores (or nano-gaps) may be useful for detecting a biomolecule, including determining the sequence of a nucleic acid molecule, such as a deoxyribonucleic acid (DNA) or ribonucleic acid (RNA) molecule. The determination of the sequence of a nucleic acid molecule may provide various benefits, such as aiding in diagnosing and/or treating a subject. For example, the nucleic acid sequence of a subject may be used to identify, diagnose and potentially develop treatments for genetic diseases.

Nano-gaps may include metalization regions, including tunneling nanoelectrodes, and particularly adjustable tunneling nanoelectrodes, which may be used for determining the sequence of a DNA or RNA strand. Production of tunneling electrodes may require large surface areas of metalization, which may need to be removed as part of a liftoff process.

SUMMARY

The present disclosure provides methods and apparatuses that may be used to create nanoelectrode systems, which may be used for molecular detection, sensing or sequencing, such as nucleic acid sequencing. Devices and systems of the present disclosure may be to sequence biopolymers, such as deoxyribonucleic acid (DNA) or ribonucleic acid (RNA).

Methods of production of production using hard mask liftoff processes are described which allow for the use of overhanging hard masks while not damaging an underlying polymeric material (e.g., polyimide) layer or other insulating layer. Tetraethyl orthosilicate (TEOS) is described for use as a part of a hard mask process, while other materials may also serve as an actual mask. The mask is described as having a number of apertures throughout large areas without metalization features, which serve to allow access by liftoff reagents to many points under the hard mask so as to allow complete lift off within a reasonable period of time. TEOS is further utilized as a substrate under apertures in areas without intended metalization features, so that metal deposited through the apertures which permit liftoff reagent access may also be lifted off.

An aspect of the present disclosure provides a method for forming a metallic material adjacent to a substrate for use in a nano-gap electrode, comprising: (a) forming a layer of a hard mask material adjacent to the substrate; (b) etching the layer of the hard mask material to form a first hole in the layer; (c) etching the layer of the hard mask material to (i) form at least one second hole in the layer of the hard mask material and (ii) remove the hard mask material in the first hole to expose the substrate, wherein the at least one second hole is adjacent to the first hole, and wherein the at least one second hole extends partially through the layer; (d) depositing the metallic material adjacent to the layer and the substrate through the first hole and second hole; and (e) removing the layer to provide the metallic material adjacent to the substrate.

In some embodiments of aspects provided herein, the substrate includes at least a first layer and a second layer. In some embodiments of aspects provided herein, the first layer is a semiconductor. In some embodiments of aspects provided herein, the semiconductor includes silicon. In some embodiments of aspects provided herein, the second layer is a semiconductor nitride. In some embodiments of aspects provided herein, the hard mask material is tetraethyl orthosilicate. In some embodiments of aspects provided herein, the hard mask is not a photoresist. In some embodiments of aspects provided herein, subsequent to the etching in (b) and before the etching in (c), the first hole extends partially through the layer of the hard mask material. In some embodiments of aspects provided herein, the etching in (b) is anisotropic etching. In some embodiments of aspects provided herein, the anisotropic etching includes resistive ion etching. In some embodiments of aspects provided herein, the etching in (c) is isotropic etching. In some embodiments of aspects provided herein, the at least one second hole includes a plurality of holes. In some embodiments of aspects provided herein, individual holes of the plurality have a diameter that is less than or equal to $(2)^{1/2}*L/2$ or $L/(3)^{1/2}$, wherein 'L' is a distance between centers of holes in the plurality. In some embodiments of aspects provided herein, individual holes of the plurality have a diameter that is greater than $(2)^{1/2}*L/2$ or $L/(3)^{1/2}$, wherein 'L' is a distance between centers of holes in the plurality. In some embodiments of aspects provided herein, the removing in (e) includes removing the layer below the metallic material at a time that is substantially the same as removing a lateral portion of the layer. In some embodiments of aspects provided herein, the metallic material comprises gold, silver or platinum. In some embodiments of aspects provided herein, the removing in (e) includes removing the metallic material adjacent to the layer.

Another aspect of the present disclosure provides a method for forming a metallic material adjacent to a substrate for use in a nano-gap electrode, comprising: (a) forming a first layer of a hard mask material adjacent to the substrate; (b) etching the first layer of the hard mask material to form a first hole and second hole through the first layer; (c) forming a second layer of the hard mask material adjacent to the first layer; (d) etching the second layer of the hard mask material to form a third hole through the second layer; (e) depositing the metallic material adjacent to the first layer and the substrate through the first hole, second hole and third hole; and (f) removing the first layer and second layer to provide the metallic material adjacent to portions of the substrate exposed through the first hole and second hole.

In some embodiments of aspects provided herein, the substrate includes a plurality of layers. In some embodiments of aspects provided herein, the substrate includes a layer of a semiconductor nitride adjacent to a layer of a semiconductor material. In some embodiments of aspects provided herein, the hard mask material is tetraethyl orthosilicate. In some embodiments of aspects provided herein, the hard mask is not a photoresist. In some embodiments of aspects provided herein, subsequent to the etching in (b), the first hole and second hole expose portions of the substrate. In some embodiments of aspects provided herein, subsequent to the etching in (c), the third hole exposes a portion of the first layer. In some embodiments of aspects provided herein, the third hole is among a plurality of holes through the second layer. In some embodiments of aspects provided herein, individual holes of the plurality are separated by a distance that is less than or equal to $(2)^{1/2}*L/2$ or $L/(3)^{1/2}$, wherein 'L' is a distance between centers of holes in the plurality. In some embodiments of aspects provided herein, individual holes of the plurality are separated by a distance that is greater than $(2)^{1/2}*L/2$ or $L/(3)^{1/2}$, wherein 'L' is a distance between centers of holes in the plurality. In some embodiments of aspects provided herein, the removing in (e) includes removing the first layer below the metallic material at a time that is substantially the same as removing a lateral portion of the first layer. In some embodiments of aspects provided herein, the metallic material comprises gold, silver or platinum. In some embodiments of aspects provided herein, the removing in (f) includes removing the metallic material adjacent to the first layer.

Another aspect of the present disclosure provides a computer readable medium comprising machine executable code that, upon execution by one or more computer processors, implements a method for forming a metallic material adjacent to a substrate for use in a nano-gap electrode, the method comprising: (a) forming a layer of a hard mask material adjacent to the substrate; (b) etching the layer of the hard mask material to form a first hole in the layer; (c) etching the layer of the hard mask material to (i) form at least one second hole in the layer of the hard mask material and (ii) remove the hard mask material in the first hole to expose the substrate, wherein the at least one second hole is adjacent to the first hole, and wherein the at least one second hole extends partially through the layer; (d) depositing the metallic material adjacent to the layer and the substrate through the first hole and second hole; and (e) removing the layer to provide the metallic material adjacent to the substrate.

Another aspect of the present disclosure provides a computer readable medium comprising machine executable code that, upon execution by one or more computer processors, implements a method for forming a metallic material adjacent to a substrate for use in a nano-gap electrode, comprising: (a) forming a first layer of a hard mask material adjacent to the substrate; (b) etching the first layer of the hard mask material to form a first hole and second hole through the first layer; (c) forming a second layer of the hard mask material adjacent to the first layer; (d) etching the second layer of the hard mask material to form a third hole through the second layer; (e) depositing the metallic material adjacent to the first layer and the substrate through the first hole, second hole and third hole; and (f) removing the first layer and second layer to provide the metallic material adjacent to portions of the substrate exposed through the first hole and second hole.

Another aspect of the present disclosure provides a computer readable medium comprising machine executable code that upon execution by one or more computer processors implements any of the methods above or elsewhere herein.

Another aspect of the present disclosure provides a computer system comprising one or more computer processors and a computer readable medium coupled thereto. The computer readable medium comprises machine executable code that upon execution by the one or more computer processors implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTIONS OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIGS. 3A-3E illustrate several side views of process steps for creating nanoelectrodes structures;

FIGS. 4A-4G illustrate several side views of process steps for creating nanoelectrode structures.

DETAILED DESCRIPTION

Figure 1:
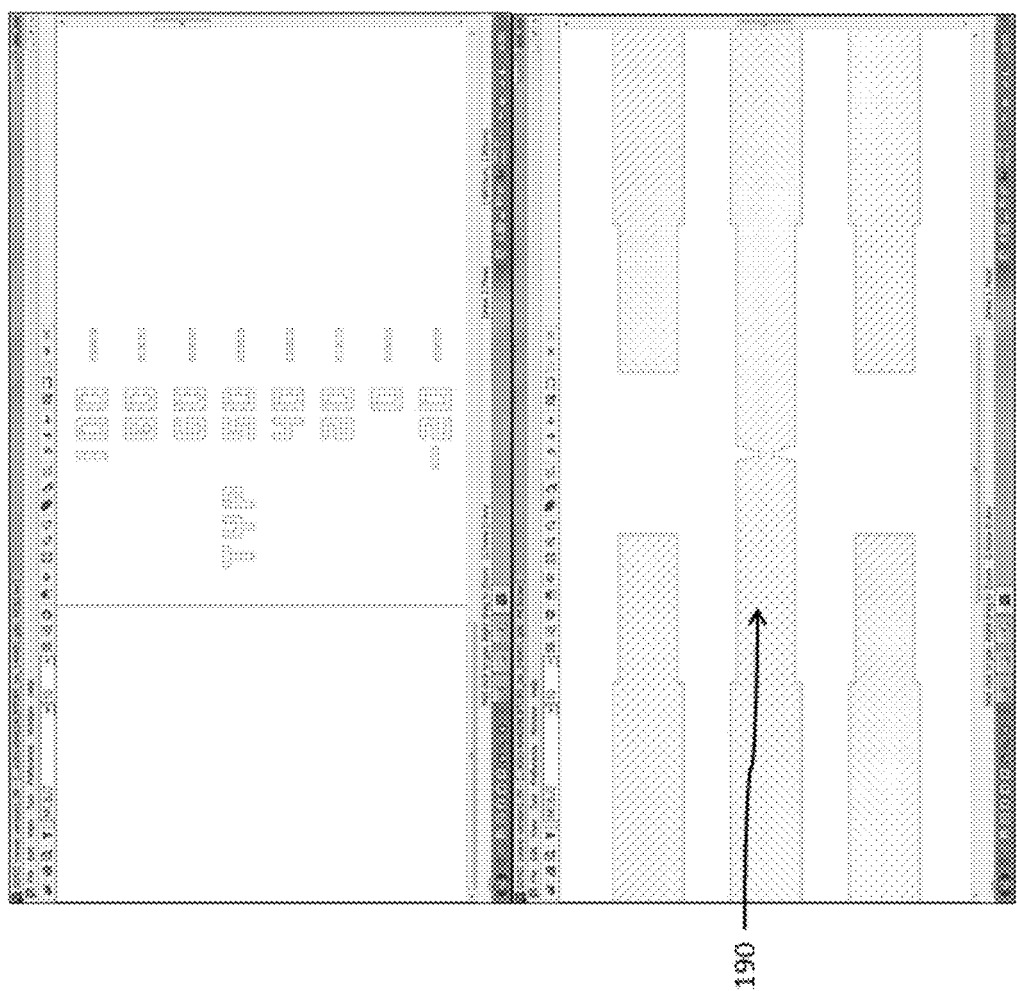
FIG. 1 illustrates a first mask pattern (or layout pattern) for a hard mask lift off fabrication process.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "gap," as used herein, generally refers to a pore, channel or passage formed or otherwise provided in a material. The material may be a solid state material, such as a substrate. The gap may be disposed adjacent or in proximity to a sensing circuit or an electrode coupled to a sensing circuit. In some examples, a gap has a characteristic width or diameter on the order of 0.1 nanometers (nm) to about 1000 nm. A gap having a width on the order of nanometers may be referred to as a "nano-gap" (also "nanogap" herein). In some situations, a nano-gap has a width that is from about 0.1 nanometers (nm) to 50 nm, 0.5 nm to 30 nm, or 0.5 nm or 10 nm, 0.5 nm to 5 nm, or 0.5 nm to 2 nm, or no greater than 2 nm, 1 nm, 0.9 nm, 0.8 nm, 0.7 nm, 0.6 nm, or 0.5 nm. In some cases, a nano-gap has a width that is at least about 0.5 nm, 0.6 nm, 0.7 nm, 0.8 nm, 0.9 nm, 1 nm, 2 nm, 3 nm, 4 nm, or 5 nm. In some cases, the width of a nano-gap can be less than a diameter of a biomolecule or a subunit (e.g., monomer) of the biomolecule.

The term "electrode," as used herein, generally refers to a material or part that can be used to measure electrical current. An electrode (or electrode part) can be used to measure electrical current to or from another electrode. In some situations, electrodes can be disposed in a channel (e.g., nanogap) and be used to measure the current across the channel. The current can be a tunneling current. Such a current can be detected upon the flow of a biomolecule (e.g., protein) through the nano-gap. In some cases, a sensing circuit coupled to electrodes provides an applied voltage across the electrodes to generate a current. As an alternative or in addition to, the electrodes can be used to measure or and/or identify the electric conductance associated with a biomolecule (e.g., an amino acid subunit or monomer of a protein). In such a case, the tunneling current can be related to the electric conductance.

The term "biomolecule," as used herein generally refers to any biological material that can be interrogated with an electrical current and/or potential across a nano-gap electrode. A biomolecule can be a nucleic acid molecule, protein, or carbohydrate. A biomolecule can include one or more subunits, such as nucleotides or amino acids.

The term "nucleic acid," as used herein, generally refers to a molecule comprising one or more nucleic acid subunits. A nucleic acid may include one or more subunits selected from adenosine (A), cytosine (C), guanine (G), thymine (T) and uracil (U), or variants thereof. A nucleotide can include A, C, G, T or U, or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a nucleic acid is deoxyribonucleic acid (DNA) or ribonucleic acid (RNA), or derivatives thereof. A nucleic acid may be single-stranded or double stranded.

The term "protein," as used herein, generally refers to a biological molecule, or macromolecule, having one or more amino acid monomers, subunits or residues. A protein containing 50 or fewer amino acids, for example, may be referred to as a "peptide." The amino acid monomers can be selected from any naturally occurring and/or synthesized amino acid monomer, such as, for example, 20, 21, or 22 naturally occurring amino acids. In some cases, 20 amino acids are encoded in the genetic code of a subject. Some proteins may include amino acids selected from about 500 naturally and non-naturally occurring amino acids. In some situations, a protein can include one or more amino acids selected from isoleucine, leucine, lysine, methionine, phenylalanine, threonine, tryptophan and valine, arginine, histidine, alanine, asparagine, aspartic acid, cysteine, glutamine, glutamic acid, glycine, proline, serin and tyrosine.

The term "layer," as used herein, refers to a layer of atoms or molecules on a substrate. In some cases, a layer includes an epitaxial layer or a plurality of epitaxial layers. A layer may include a film or thin film. In some situations, a layer is a structural component of a device (e.g., light emitting diode) serving a predetermined device function, such as, for example, an active layer that is configured to generate (or emit) light. A layer generally has a thickness from about one monoatomic monolayer (ML) to tens of monolayers, hundreds of monolayers, thousands of monolayers, millions of monolayers, billions of monolayers, trillions of monolayers, or more. In an example, a layer is a multilayer structure having a thickness greater than one monoatomic monolayer. In addition, a layer may include multiple material layers (or sub-layers). In an example, a multiple quantum well active layer includes multiple well and barrier layers. A layer may include a plurality of sub-layers. For example, an active layer may include a barrier sub-layer and a well sub-layer.

The term "adjacent" or "adjacent to," as used herein, includes 'next to', 'adjoining', 'in contact with', and 'in proximity to'. In some instances, adjacent to components are separated from one another by one or more intervening layers. For example, the one or more intervening layers can have a thickness less than about 10 micrometers ("microns"), 1 micron, 500 nanometers ("nm"), 100 nm, 50 nm, 10 nm, 1 nm, or less. In an example, a first layer is adjacent to a second layer when the first layer is in direct contact with the second layer. In another example, a first layer is adjacent to a second layer when the first layer is separated from the second layer by a third layer.

The term "substrate," as used herein, refers to any workpiece on which film or thin film formation is desired. A substrate includes, without limitation, silicon, germanium, silica, sapphire, zinc oxide, carbon (e.g., graphene), SiC, AN, GaN, spinel, coated silicon, silicon on oxide, silicon carbide on oxide, glass, gallium nitride, indium nitride, titanium dioxide and aluminum nitride, a ceramic material (e.g., alumina, AlN), a metallic material (e.g., molybdenum, tungsten, copper, aluminum), and combinations (or alloys) thereof. A substrate can include a single layer or multiple layers.

The present disclosure provides methods for fabricating electrodes for use in devices and systems for sensing biomolecules, such as nucleic acid molecules. Devices of the present disclosure can include nano-gap electrodes, which can be used to detect a tunneling current across a gap. Such electrodes can be part of an array of electrodes and can be coupled to a computer system having one or more computer processors that are programmed to detect biomolecules using signals detected by the electrodes. Such signals can be current, such as tunneling current.

Electrodes can be formed using a series of fabrication operations. Such fabrication operations can be performed in a controlled environment, such as under vacuum or under the flow of an inert gas (e.g., He, Ar, or $N_2$).

FIG. 1 illustrates a first mask for regions corresponding to where electrode structures will be fabricated. It can be observed that the size of the corresponding features in FIG. 2 can be slightly smaller than those of FIG. 1, as first mask regions allow for space for a titanium layer where it comes into contact with a layer of a polymeric material, such as polyimide-isoindoloquinazolinedione (PiQ), and a space between the titanium layer and an electrode. The mask may be a mask for a negative photoresist, resulting in removal of photo resist material, and ultimately in removal, which may be by an aqueous process, of tetraethyl orthosilicate (Si$(OC_2H_5)_4$, TEOS) in regions with opaque mask features 190. A TEOS layer corresponding to this mask may be referred to as a cover layer or first TEOS layer.

Figure 2:
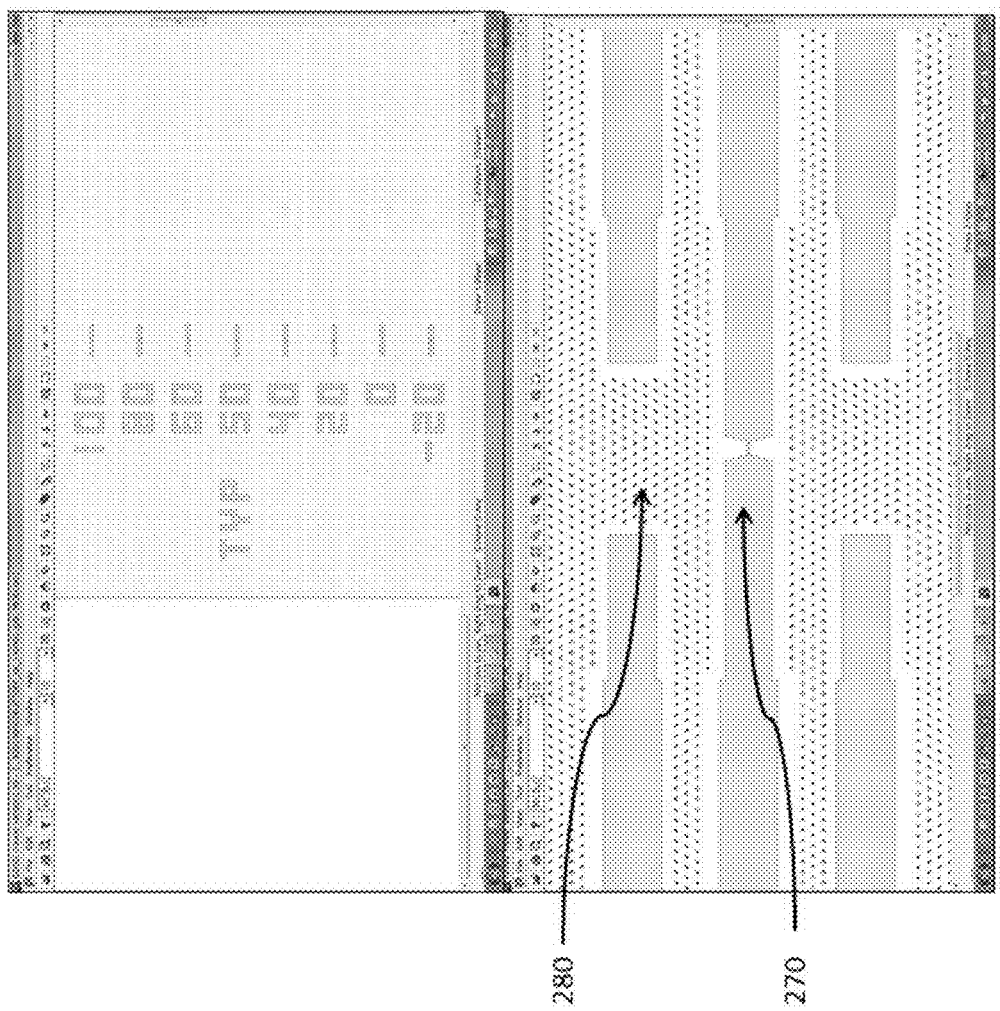
FIG. 2 illustrates a second mask pattern (or layout pattern) for a hard mask lift off fabrication process.

FIG. 2 illustrates a second mask including a center electrode 270, which may later be fractured to form an electrode pair, which may be adjusted to set the spacing between two members of a formed center electrode pair. The mask depicted in FIG. 2 may also be a mask for a negative photoresist, which can result in the removal of photo resist material, and ultimately in removal of first TEOS layer below photo resist, such as immediately below the photo resist. Above and below center electrode may be two pairs of other electrodes. Depicted in FIG. 2 in otherwise clear areas is an array of spots or apertures in a "dummy" pattern 280; the dummy pattern may be used to create a set of holes in overlying layers of titanium and TEOS, permitting a liftoff process to readily remove these layers, and thence underlying TEOS layers. An array of dummy pattern 280 may incidentally create an array of metallization layer features. The dummy pattern can include features that may be disc shaped and may need to be removed, as part of the liftoff process.

Although dummy apertures and associated metal patterns are depicted in FIG. 2 and FIGS. 3A-3E as having a smaller diameter than a distance between centers of the discs minus a diameter of the discs, a diameter of a disc associated with an aperture and associated metal patterns may be greater than a distance between centers of the discs minus a diameter of the discs. This may minimize the time needed to etch under the discs and metal deposited on second TEOS layer.

In some embodiments, illustrating the situation for a square "dummy" pattern grid, a disc diameter D may be less than or equal to sqrt(2) times a distance between centers of discs L divided by 2, which distance makes a distance to etch to a center of a disc the same as a distance to etch to the area farthest from a disc. The disc diameter D can have a tolerance of +/−1%, 5%, 10%, or 15%.

In some embodiments, illustrating a situation for a hexagonal close pack "dummy" pattern grid, a disc (or spot) diameter D may be less than or equal to a distance between centers L divided by sqrt(3), which distance makes a distance to etch to a center of a disc the same as a distance to etch to an area farthest from a spot. The disc diameter D can have a tolerance of +/−1%, 5%, 10%, or 15%.

In further embodiments, disc diameters D may be greater than sqrt(2) times a distance between centers of discs L divided by 2 or L divided by sqrt(3), as an area to be etched may be greater for metal regions deposited on second TEOS layer than on disc shaped metal deposited on first TEOS layer, as etching reagents may have their etching effectiveness diminished as more material is etched and greater distances are needed to diffuse back to a larger reagent volume above metalization layers. The disc diameter D can have a tolerance of +/−1%, 5%, 10%, or 15%.

Although a dummy region depicted in FIG. 2 is shown as a having a number of disc shaped regions, many other shapes may be utilized, including, rectangles, lines, ovals, circles, spirals, crossing lines, concentric lines following the outlines of areas which are to become electrodes, or any other shape or combination of shapes. A maximum width of an aperture may, however, desirously be made with some limitations, wherein any metalization regions which may be formed may on a first TEOS layer may be readily removed at the time of a liftoff process. In some embodiments, it may be desirable to utilize a large number of apertures, which may be closely spaced to minimize etching time and maximize liftoff without retention.

In an aspect, a method for forming a metallic material adjacent to a substrate for use in a nano-gap electrode comprises forming a first layer of a hard mask material adjacent to the substrate and etching the first layer of the hard mask material to form a first hole and second hole through the first layer. The first hole and second hole can expose portions of the substrate.

Next, a second layer of the hard mask material (or a different hard mask material) can be formed adjacent to the first layer. In some cases, the third hole exposes a portion of the first layer.

Next, the second layer of the hard mask material can be etched to form a third hole through the second layer. The metallic material can then be deposited adjacent to the first layer and the substrate through the first hole, second hole and third hole.

Next, the first layer and second layer can be removed to provide the metallic material adjacent to portions of the substrate exposed through the first hole and second hole. Removal of the first layer can include removing the metallic material adjacent to the first layer.

In some cases, the first layer is removed by etching. Such etching can provide etching times below the metallic material (e.g., disc) that is adjacent to the first layer and other metallic material laterally disposed in relation to the metallic material and adjacent to the first layer that are the same or substantially the same, or within about 1%, 5%, 10%, or 50% of one another. This can permit a portion of the first layer below the metallic material to be removed at the same or substantially the same time as a lateral portion (e.g., along a vector that is parallel to a surface of the substrate) of the first layer (e.g., portion of the first layer between the metallic material), which can permit the first layer to be efficiently removed.

The substrate can be formed of a semiconductor material, such as, for example, silicon. The substrate can include at least a first layer and a second layer. The first layer can include a semiconductor (e.g., silicon) and the second layer can include a semiconductor nitride, such as, for example, silicon nitride.

The hard mask material can be or include an inorganic or organometallic etch barrier layer, which can be deposited, for example, by chemical vapor deposition (CVD), physical vapor deposition (PVD) or spin-coating processes over the top of a thicker layer, which in some cases is high in carbon content (e.g., a carbon hard mask). Some examples of CVD hard mask layers include SiON, SiN, and TiN. Organosilicates are one example of a spin-on hard mask. An example of a carbon hard mask applied by CVD is alpha-carbon. Spin-on carbon (SOC) hard mask layers consist of organic polymer solutions that are high in carbon content by design.

A hard mask can be a single layer or multilayer (e.g., at least 2, 3, 4, 5, 6, 7, 8, 9 or 10 layers) structure. In an example, the hard mask is or includes tetraethyl orthosilicate (TEOS).

In some examples, the hard mask is not a photoresist. In such a case, the hard mask may not be reactive or substantially reactive to a source of activation, such as light (e.g., ultraviolet light) or an electron beam. Thus, a hard mask may maintain its chemical and physical structure upon exposure to light or an electron beam.

The third hole can include a plurality of holes, such as at least 2, 3, 4, 5, 6, 7 8, 9, 10, 50, 100, 500, or 1000 holes. Such holes can be "dummy" holes, as described elsewhere herein. Individual holes of the plurality have a diameter that is less than or equal to $(2)^{1/2}*L/2$ or $L/(3)^{1/2}$, wherein 'L' is a distance between centers of holes in the plurality. As an alternative, individual holes of the plurality have a diameter that is greater than $(2)^{1/2}*L/2$ or $L/(3)^{1/2}$, wherein 'L' is a distance between centers of holes in the plurality. Such diameters can have tolerances of +/−1%, 5%, 10%, or 15%.

The metallic material can include a material that has high electrical conductivity. In some cases, the metallic material is formed of gold, silver, platinum or an alloy thereof.

FIG. 3A illustrates the first portion of a process for generating nanoelectrodes or arrays of nanoelectrodes. Arrays may be a two dimensional array or a three dimensional array, wherein a two dimensional array may comprise pairs of opposing electrodes and associated electrode tips, wherein a nanochannel may be interposed.

In some embodiments, a first operation for a process for fabrication for nano electrodes may comprise depositing a first layer 300, which may comprise a precursors to PiQ (polyimide-isoindoloquinazolinedione) layer, which may subsequently be baked, where in bake temperature say be variable, and may increase from 150 C to 250 C. Polyimide first layer 300 may have subsequent process operations effectuated so as to create a nanochannel between members of a pair of electrodes. Such a layer of polyimide may be deposited using a CVD (Chemical Vapor Deposition) process, or may be applied using a spin coating technique, or may be applied using any other appropriate method. First layer is herein described as comprising polyimide, but other materials may be utilized as appropriate.

A substrate underlying polyimide first layer 300 may be silicon, gallium, or other suitable semiconductor or combination of semiconductor substrates, or may be an oxide substrate, such as $SiO_2$. A substrate may be a doped substrate so as to enable proper usage on an e-beam lithography process, wherein doping may prevent charge buildup. Alternatively, portions of the substrate may be made conductive, for example by doping, wherein a dopant implant may be limited to regions wherein fine resolution may be needed and any regions needed to provide electrical connection to such regions. As a further alternative, metalization patterns may be effectuated corresponding to regions wherein areas needing fine features may otherwise have a resolution of fan e-beam degraded such that the e-beam may not be able to form the fine features. Additionally, features may be patterned using excimer lasers or using phase masks and associated ultraviolet sources as appropriate to the size of the features.

In some embodiments, wherein a nanochannel may be less than 100 nm in depth, a thickness of a first layer 300, which may be a PiQ first layer 300, may be more than 100 nm, and may be as thick as several microns in thickness, or may be any thickness between 100 nm and several microns, such as 400 nm, 800 nm, 2 microns, 5 microns, and 10 microns. A same process may be used to make larger metallic features 350.

In other embodiments, other material(s) may be utilized as a first layer 300, which may be, for example silicon nitride, silicon oxide, or other standard semiconductor materials, which may be nonconductive, have a high dielectric, and may have an electrical conductivity of $10^{12}$ ohm centimeters or more. The material may be selected in combination with an etching process such that the underlying layer is not damaged as a result of an etching process used as a part of the lift off methodology. Thus if an organic polymer is selected as an underlying layer, the use of organic solvents may be incompatible.

A first TEOS (tetraethylorthosilicate) layer 320 may be deposited, and may be deposited in a thickness which may be 100 nm. A first TEOS layer may be of a thickness which permits ready etching of the first TEOS layer so as to permit liftoff of metalization as a part of a dummy pattern, and may be from 50 to 100 nm in thickness, or may be from 25 to 50 nm in thickness, or may be from 100 to 250 nm in thickness, or may be greater than 250 nm in thickness, or may be less than 25 nm in thickness.

A first TEOS layer 320 may be annealed. A first TEOS layer 320 may then have a resist layer 310 coated thereupon, which may be patterned using the mask depicted in FIG. 1. Regions wherein a first TEOS layer may be removed 321 may be regions wherein in future operations, electrodes may be formed. A resist mask material may be an e-beam resist, a photolithography resist, or a combination thereof, wherein an e-beam resist may be utilized for regions which require smaller features than be readily effectuated by a more standard photo lithography resist. If two different resist types and processes are utilized, either may be performed first.

The TEOS may thence be removed from those regions which are not covered by the resist, wherein the removal process may be an etch process, and may be a wet etch process or a vapor etch process, and may utilize hydrogen fluoride (HF), hot phosphoric acid, hydrogen peroxide, or any other appropriate etching method and material. The removal process may employ anisotropic (or directional) etching, such as, for example, resistive ion etching (RIE) or plasma etch with, for example, $CF_4$, $CHF_3$, or $C_4F_8$.

FIG. 3B illustrates a second portion of a process for generating nanoelectrodes, which may include the removal of the resist layer 310 depicted in FIG. 3A. A titanium layer 330, which may be 100 nm in thickness, 50 nm to 100 nm in thickness, less than 50 nm in thickness, 100 nm to 250 nm in thickness, 200 nm in thickness, or greater than 250 nm in thickness, but may be thicker or thinner as needed for formation of electrodes as described herein below may thence be applied to the surface, covering both exposed portions of the PiQ layer 300 and remaining (non-etched) portions of the TEOS layer 320. Although titanium is described herein, alternative metals may be utilized, preferably those metals which may be routinely used for semiconductor processing, and which may be etched using materials and processes which do not etch TEOS. Similarly, other materials other than metals may be utilized in place the titanium layer, including silicon nitride.

A second TEOS layer 322 may thence be applied to the titanium layer 330, potentially covering the entire titanium layer 330. A second resist layer 311 may then be applied and imaged using the second mask as depicted in FIG. 2. The TEOS may then be removed in those areas which are not masked by the second patterned resist layer 323. The mask may have spots or apertures corresponding to areas wherein electrodes may be formed, and may also have spots or apertures corresponding to "dummy" areas, which may be useful for removing large areas during a liftoff process. These dummy areas will be further described herein below. The dummy regions are the two smaller center apertures.

FIG. 3C illustrates a third portion of a process for generating nanoelectrodes, which may include initially removing the second resist layer 311. A wet etch of the titanium layer 330 may then be performed, which may serve to undercut the additional second TEOS 322 layer slightly, leaving apertures in titanium layer 331. Etchant conditions may determine how much of an undercut is created, wherein etchant conditions may include time, temperature, and concentration of etchant reagents. TEOS may form a $SiO_2$ layer on TEOS surfaces of second TEOS layer 322 which may interact with wet etchant during a wet etching process. A further bake of PiQ layer 300 may then be performed to remove any aqueous phase which may remain from etching and subsequent cleaning processes. Etchant reagents may be determined depending upon other materials utilized for various layers utilized in a structure.

An undercut of second TEOS layer 322 serves to provide later access to both TEOS layers at a region of an undercut, permitting a liftoff process to function well, whereas otherwise the later applied metals may cover TEOS layers preventing liftoff reagents from having access to TEOS layers.

FIG. 3D illustrates a fourth portion of a process for generating nanoelectrodes, which may include deposition of a chromium adhesion layer and a gold layer 340, wherein the chromium and gold may be deposited slightly under the second TEOS layer 322. The chromium and gold layer 340 may be applied using sputtering or other appropriate metal deposition methods.

Other adhesion materials may be utilized in place of chromium, including chromium oxide, titanium, titanium oxide, aluminum, aluminum oxide, tantalum, tantalum oxide, indium tin oxide, chalcogenide glasses, or any other appropriate material. Other metals may be utilized in place of gold as a part of an electrode, including platinum, palladium, rhodium, iridium, osmium, tantalum, niobium, or other inert materials.

A thickness of chromium may be any desired thickness suitable for adhering gold or other metals to the polyimide or other insulating materials which may be later utilized to form a channel. Chromium or other adhesion materials and or gold layer 340 or other metals may be applied in part in regions underneath the TEOS, but may leave a gap between the chromium and gold layer 340 and the second TEOS layer 322, thus allowing liftoff reagents access to the second TEOS layer 322 in later parts of processes as described herein. Thus the combined thickness of the adhesion layer and the metal utilized for the electrode may not be of thickness sufficient to prevent reagent access to the second TEOS layer 322. A gap between gold layer 320 and second TEOS layer 322 may be a gap of 5 to 25 nm, 25 to 50 nm, or greater than 50 nm.

FIG. 3E illustrates a fifth portion of a process for fabricating nanoelectrodes, which may include a lift off process, which may utilize a HF (hydrofluoric acid) etch or other appropriate reagents appropriate as an etchant for TEOS as described hereinabove, leaving chromium and gold layer 340 on the PiQ layer 300. A back grind may then be performed to reduce the thickness of the substrate (not shown). Alternatively, a thinned wafer may be utilized throughout the processes described hereinabove.

In another aspect, a method for forming a metallic material adjacent to a substrate for use in a nano-gap electrode comprises forming a layer of a hard mask material adjacent to the substrate and etching the layer of the hard mask material to form a first hole in the layer. In some cases, the first hole extends partially through the layer of the hard mask material. The etching can be anisotropic (or directional) etching. An example of anisotropic etching is resistive ion etching or plasma etching with, for example, $CF_4$, $CHF_3$, or $C_4F_8$.

Next, the layer of the hard mask material can be etched to (i) form at least one second hole (e.g., at least 1, 2, 3, 4, 5, 6, 7 8, 9, 10, 50, 100, or 500 second holes) in the layer of the hard mask material and (ii) remove the hard mask material in the first hole to expose the substrate. The at least one second hole can be adjacent to the first hole. The at least one second hole extends partially through the layer. Etching in such a case can be isotropic etching.

Next, the metallic material can be deposited adjacent to the layer and the substrate through the first hole and second hole. The layer can then be removed to provide the metallic material adjacent to the substrate. Removal of the layer can include removing the metallic material adjacent to the layer.

In some cases, the layer is removed by etching. Such etching can provide etching times below the metallic material (e.g., disc) that is adjacent to the layer and other metallic material laterally disposed in relation to the metallic material and adjacent to the layer that are the same or substantially the same, or within about 1%, 5%, 10%, or 50% of one another. This can permit a portion of the layer below the metallic material to be removed at the same or substantially the same time as a lateral portion (e.g., along a vector that is parallel to a surface of the substrate) of the layer (e.g., portion of the first layer between the metallic material), which can permit the first layer to be efficiently removed.

The at least one second hole can include a plurality of holes, such as at least 2, 3, 4, 5, 6, 7 8, 9, 10, 50, 100, 500, or 1000 second holes. Such holes can be "dummy" holes, as described elsewhere herein. Individual holes of the plurality have a diameter that is less than or equal to $(2)^{1/2}*L/2$ or $L/(3)^{1/2}$, wherein 'L' is a distance between centers of holes in the plurality. As an alternative, individual holes of the plurality have a diameter that is greater than $(2)^{1/2}*L/2$ or $L/(3)^{1/2}$, wherein 'L' is a distance between centers of holes in the plurality. Such diameters can have tolerances of +/−1%, 5%, 10%, or 15%.

The metallic material can include a material that has high electrical conductivity. In some cases, the metallic material is formed of gold, silver, platinum or an alloy thereof.

The substrate can be formed of a semiconductor material, such as, for example, silicon. The substrate can include at least a first layer and a second layer. The first layer can include a semiconductor (e.g., silicon) and the second layer can include a semiconductor nitride, such as, for example, silicon nitride.

The hard mask material can be or include an inorganic or organometallic etch barrier layer, which can be deposited, for example, by CVD, PVD or spin-coating processes over the top of a thicker layer, which in some cases is high in carbon content (e.g., a carbon hard mask). Some examples of CVD hard mask layers include SiON, SiN, and TiN. Organosilicates are one example of a spin-on hard mask. An example of a carbon hard mask applied by CVD is alpha-carbon. Spin-on carbon (SOC) hard mask layers consist of organic polymer solutions that are high in carbon content by design.

A hard mask can be a single layer or multilayer (e.g., at least 2, 3, 4, 5, 6, 7, 8, 9 or 10 layers) structure. In an example, the hard mask is or includes TEOS.

In some examples, the hard mask is not a photoresist. In such a case, the hard mask may not be reactive or substantially reactive to a source of activation, such as light (e.g., ultraviolet light) or an electron beam. Thus, a hard mask may maintain its chemical and physical structure upon exposure to light or an electron beam.

Figure 4A:
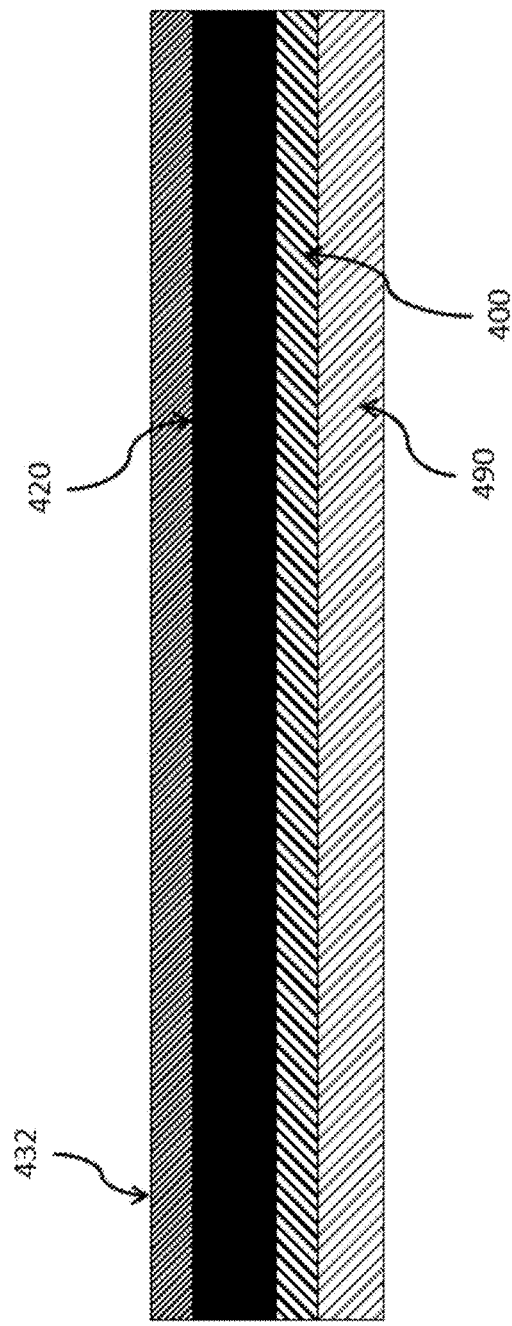

FIG. 4A illustrates a first operation of a process for fabricating nanoelectrodes, wherein a substrate 490, may have a number of layers applied to the substrate 490, including an optional underlying layer 400, which may be a PiQ layer, or other polymers, which may be useful for producing a fluidic channel structure, or may be other more standard semiconductor materials such as $SiO_2Si_3N_4$, or any other standard semiconductor material as described herein, and may be of any thickness, particularly as described herein with respect to FIG. 3 PiQ layer 300.

A TEOS 420 layer may then applied of optional underlying layer 400, wherein a thickness of the TEOS layer may be 300 nm, or may be any thickness as described hereinabove with respect to FIG. 3 second TEOS layer 322. A top layer 432, which may be a $Si_3N_4$ layer may be applied on the TEOS layer 420. The top layer 432 may have a thickness of 30 nm, but may be of any thickness as appropriate, such as 5 nm to 20 nm, 20 nm to 50 nm, 50 nm to 200 nm, or more than 200 nm.

In some embodiments, a desired or predetermined thickness for the TEOS layer 420 may be greater than may be possible using a photoresist for a given feature size, while a TEOS layer may be made thicker as a result of utilizing an anisotropic etch. Using an immersion imaging photolithographic process, a large solid angle of light may be utilized, which may be incapable of being utilized with a thick photoresist to form features with a fine features size. The smallest feature size and thickest photoresist layer are typically closely linked.

FIG. 4B illustrates an additional operation in a process for fabricating nanoelectrodes, wherein a resist layer 410 may be applied on top layer 432, and may be patterned using any standard lithography process, leaving a large aperture on the right side of FIG. 4B, which may be useful for forming a nanoelectrode. An dry etch process is then utilized, wherein the top layer 432 is etched through, and TEOS layer 420 is partly etched through, leaving a portion of TEOS layer 420 on optional underlying layer 400. In some embodiments, TEOS layer may be etched completely through, particularly when partial etching of optional underlying layer 400 or substrate 490 is acceptable.

FIG. 4C illustrates an additional operation in a process for fabricating nanoelectrodes, wherein resist layer 410 may have been removed, and a large aperture suitable for forming a nano electrode is shown on the right of FIG. 4C.

Figure 4D:
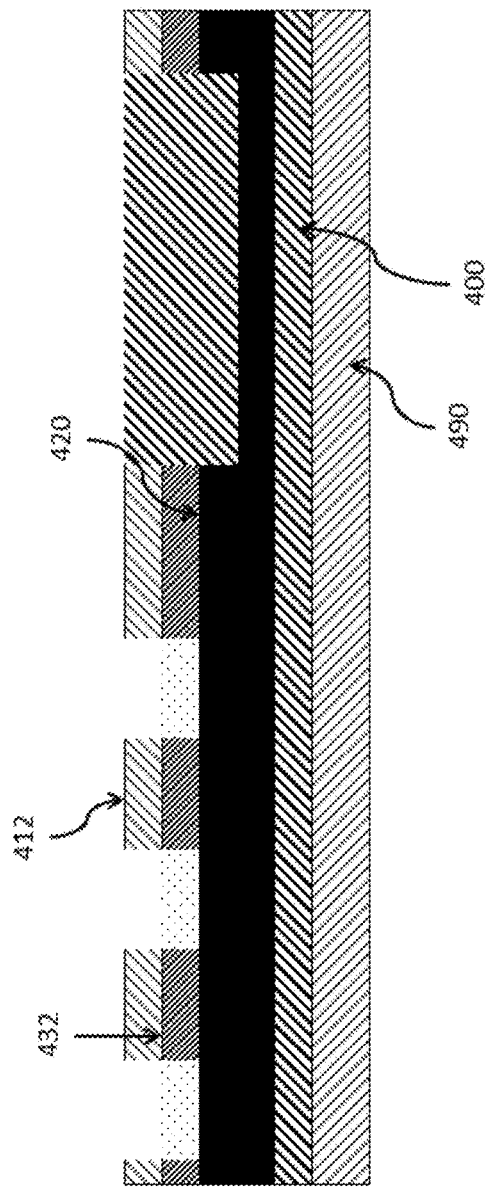

FIG. 4D illustrates an additional operation in a process for fabricating nanoelectrodes, wherein an a second resist layer 412 may be formed on top layer 432, and in the large aperture on the right side of FIG. 4D which may be suitable for forming nanoelectrodes. The second resist layer 412 may be patterned using any standard lithography process, and apertures for dummy patterns, the size of which were describe hereinabove, may be etched through top layer 432.

Figure 4E:
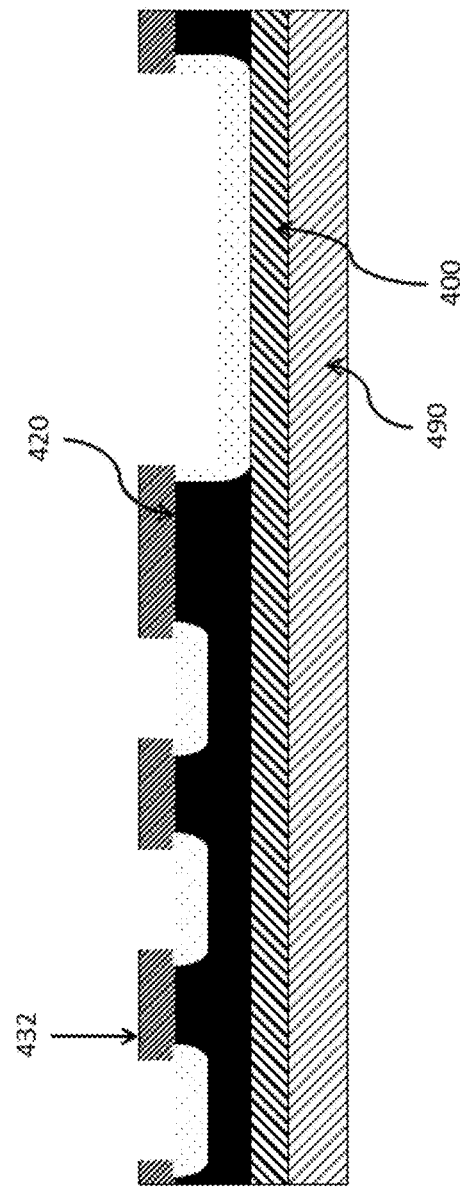

FIG. 4E illustrates an additional operation in a process for fabricating nanoelectrodes, wherein a wet etch process is utilized to etch TEOS layer, while the wet etch may not etch optional underlying layer 400. The wet etch may partially etch TEOS layer 420 in regions for dummy patterns, for example as shown on the left three apertures of FIG. 4E, leaving a thickness of TEOS layer 420 appropriate for efficient later etching in a subsequent lift-off process to be described hereinafter of remaining TEOS layer 420 under a metal layer to be applied later to TEOS layer 420, while etching sufficient material from the TEOS layer 420 as to allow access for etching of the TEOS layer 420 above the metal layer to be described hereinafter. The wet etch may undercut top layer 432 at the circumference of a dummy patterns. Any large apertures suitable for forming of nanoelectrodes as shown on the right side of FIG. 4E may have regions of the top layer 432 at the circumference of the large aperture undercut as a part of the wet etch.

FIG. 4F illustrates an additional operation in a process for fabricating nanoelectrodes, wherein a metal layer 440 may be applied to remaining top layer 432, unetched portions of TEOS layer 420 in regions of dummy patterns, and exposed optional underlying layer 400, or substrate 490 in large apertures suitable for forming nanoelectrodes. The underlying layer 400 may be a nitride, such as silicon nitride. In some embodiments, the metal layer may comprise an adhesion layer, such as chromium, which may aid in attaching an additional electrode metal, which may be gold.

FIG. 4G illustrates an additional operation in a process for fabricating nanoelectrodes, wherein a liftoff process may be performed to remove any remaining TEOS layer 420, any remaining top layer 432, and metal regions of metal layer 440 which may have been formed on remaining TEOS layer 420, or on remaining top layer 432, while leaving metal regions of metal layer 440 which may have been formed on exposed optional underlying layer 400 or substrate 490.

Thus FIG. 4G shows a formed nanoelectrode made from metal layer 440 in an intended region on optional underlying layer 400 or substrate 490.

Although various embodiments for methods of fabrication hereinabove are described as being useful for creating nanoelectrodes, these may be utilized for various other purposes wherein a liftoff process may be useful, for, for example metalization structures of various kinds.

Methods for Forming Device Layers

Methods for forming electrodes of the present disclosure can include providing a substrate in a reaction space and forming one or more layers on the substrate. The reaction space can be in a reaction chamber, such as a vacuum chamber or a chamber that is in a controller environment, such an inert gas environment.

The reaction chamber may be a vacuum chamber configured for thin film formation. The vacuum chamber, in some cases, is an ultrahigh vacuum (UHV) chamber. In cases in which a low-pressure environment is desired, the reaction chamber may be pumped with the aid of a pumping system having one or more vacuum pumps, such as one or more of a turbomolecular ("turbo") pump, a diffusion pump and a mechanical pump. The reaction chamber may include a control system for regulating precursor flow rates, substrate temperature, chamber pressure, and the evacuation of the chamber.

Growth conditions are adjustable based upon the selection of one or more process parameters for forming electrodes. Growth conditions can be selected from one or more of growth temperature, carrier gas flow rate, precursor flow rate, growth rate and growth pressure.

Layers for forming device of the present disclosure can be formed upon exposure of the substrate or layers over the substrate to various precursors of material that form the layers. Various source gases (or precursors) may be used with methods described herein. Tetraethyl orthosilicate (TEOS) can be formed via the reaction $SiCl_4 + 4C_2H_5OH \rightarrow Si(OC_2H_5)_4 + 4HCl$. $SiCl_4$ and $C_2H_5OH$ may be provided in the gas phase.

In some cases, one or more precursors are provided to a reaction chamber with the aid of a carrier gas, such as one or more of He, Ar, $N_2$ and $H_2$. The flow rate of the carrier gas during the formation of the active layer may be between about 1 liter/minute and 20 liters/minute.

Layers may be formed with the aid of various deposition techniques. Layers may be formed with the aid of chemical vapor deposition (CVD), atomic layer deposition (ALD), plasma enhanced CVD (PECVD), plasma enhanced ALD (PEALD), metal organic CVD (MOCVD), hot wire CVD (HWCVD), initiated CVD (iCVD), modified CVD (MCVD), vapor axial deposition (VAD), outside vapor deposition (OVD) and physical vapor deposition (e.g., sputter deposition, evaporative deposition). In some examples, metal layers are deposited by physical vapor deposition, such as sputtering.

Features and patterns of features can be formed using photolithography. For example, light can be used to transfer a geometric pattern from a photomask to a light-sensitive chemical "photoresist," (or resist) over a substrate. A series of chemical treatments can then transfer the exposure pattern into or enable deposition of a new material in the desired pattern upon the material underneath the photoresist. Such chemical treatments can include etching and annealing (e.g., annealing at a temperature of at least about 400° C.).

Computer Control Systems

Figure 5:
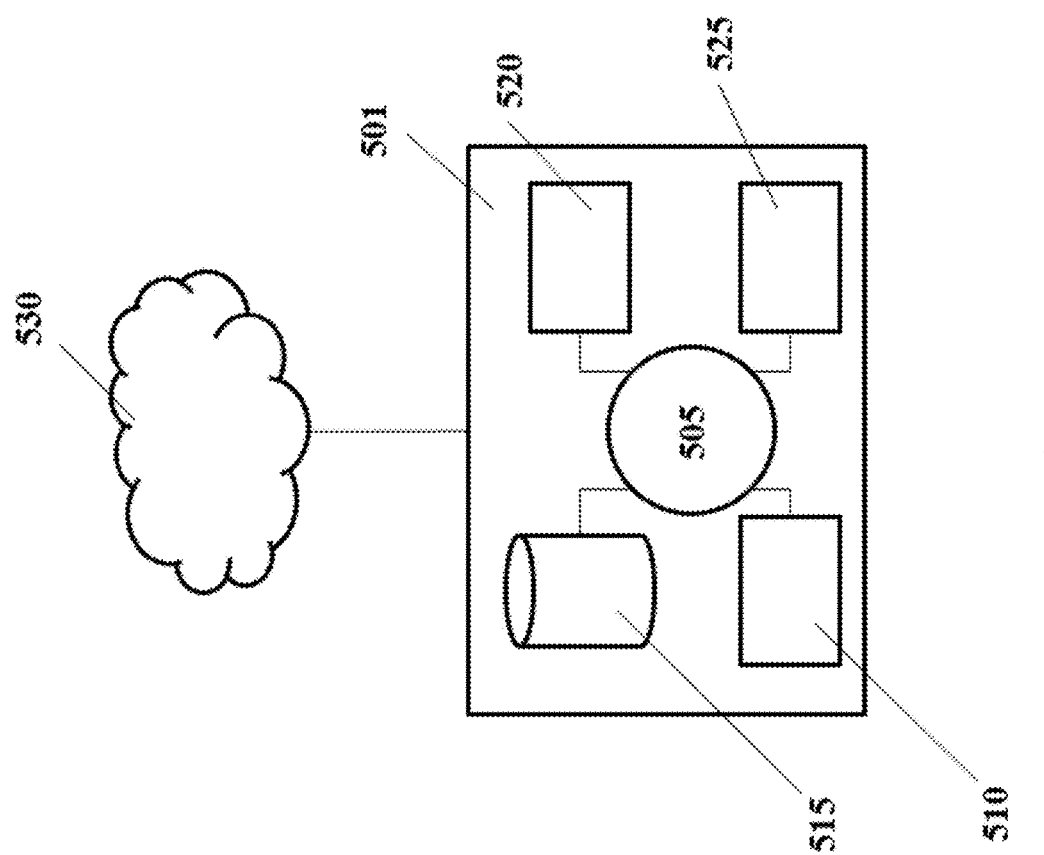
FIG. 5 shows a computer system that is programmed or otherwise configured to implement methods of the present disclosure.

The present disclosure provides computer control systems that are programmed to implement methods of the disclosure. FIG. 5 shows a computer system 501 that is programmed or otherwise configured to fabricate electrodes for use in sensing biomolecules. The computer system 501 can regulate various aspects of methods of the present disclosure, such as, for example, the formation of various device layers.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet. The network 530 in some cases is a telecommunication and/or data network. The network 530 can include one or more computer servers, which can enable distributed computing, such as cloud computing. The network 530, in some cases with the aid of the computer system 501, can implement a peer-to-peer network, which may enable devices coupled to the computer system 501 to behave as a client or a server.

The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present disclosure. Examples of operations performed by the CPU 505 can include fetch, decode, execute, and writeback.

The CPU 505 can be part of a circuit, such as an integrated circuit. One or more other components of the system 501 can be included in the circuit. In some cases, the circuit is an application specific integrated circuit (ASIC).

The storage unit 515 can store files, such as drivers, libraries and saved programs. The storage unit 515 can store user data, e.g., user preferences and user programs. The computer system 501 in some cases can include one or more additional data storage units that are external to the computer system 501, such as located on a remote server that is in communication with the computer system 501 through an intranet or the Internet. The computer system 501 can communicate with one or more remote computer systems through the network 530.

Methods as described herein can be implemented by way of machine (e.g., computer processor) executable code stored on an electronic storage location of the computer system 501, such as, for example, on the memory 510 or electronic storage unit 515. The machine executable or machine readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processer adapted to execute the code, or can be compiled during runtime. The code can be supplied in a programming language that can be selected to enable the code to execute in a pre-compiled or as-compiled fashion.

The computer system 501 can be programmed or otherwise configured to regulate one or more processing parameters, such as the substrate temperature, precursor flow rates, growth rate, carrier gas flow rate and reaction chamber pressure. The computer system 501 can be in communication with valves between the storage vessels and a reaction chamber, which can aid in terminating (or regulating) the flow of a precursor to the reaction chamber.

The computer system 501 can be in communication with a vacuum system comprising a vacuum chamber, flow valves and a pumping system. The vacuum system can include one or more vacuum pumps, such as one or more of a turbomolecular ("turbo") pump, a diffusion pump and a mechanical pump. A pump may include one or more backing pumps. For example, a turbo pump may be backed by a mechanical pump.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Methods and systems of the present disclosure can be implemented by way of one or more algorithms. An algorithm can be implemented by way of software upon execution by the central processing unit 505.

Devices, systems and methods of the present disclosure may be combined with and/or modified by other devices, systems, or methods, such as those described in, for example, JP 2013-36865A, US 2010/0025249, US 2012/0193237, US 2012/0322055, US 2013/0001082, US 2014/0300339, JP 2011-163934A, JP 2005-257687A, JP 2011-163934A and JP 2008-32529A, each of which is entirely incorporated herein by reference.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for forming a metallic material adjacent to a substrate for use in a nano-gap electrode, comprising:
    (a) forming a single layer of a hard mask material adjacent to said substrate, wherein said hard mask is not a photoresist;
    (b) etching said single layer of said hard mask material to form a first hole in said layer;
    (c) etching said single layer of said hard mask material to (i) form at least one second hole in said single layer of said hard mask material and (ii) remove said hard mask material in said first hole to expose said substrate, wherein said at least one second hole is adjacent to said first hole, and wherein said at least one second hole extends partially through said single layer;
    (d) depositing said metallic material over said substrate and over a portion of said single layer of said hard mask material; and
    (e) removing said single layer of said hard mask material to provide said metallic material adjacent to said substrate.

2. The method of claim 1, wherein said substrate includes at least a first layer and a second layer.

3. The method of claim 2, wherein said first layer is a semiconductor.

4. The method of claim 3, wherein said semiconductor includes silicon.

5. The method of claim 2, wherein said second layer is a semiconductor nitride.

6. The method of claim 1, wherein said hard mask material is tetraethyl orthosilicate.

7. The method of claim 1, wherein subsequent to said etching in (b) and before said etching in (c), said first hole extends partially through said single layer of said hard mask material.

8. The method of claim 1, wherein said etching in (b) is anisotropic etching.

9. The method of claim 8, wherein said anisotropic etching includes resistive ion etching.

10. The method of claim 1, wherein said etching in (c) is isotropic etching.

11. The method of claim 1, wherein said at least one second hole includes a plurality of holes.

12. The method of claim 11, wherein individual holes of said plurality have a diameter that is less than or equal to $(2)^{1/2}*L/2$ or $L/(3)^{1/2}$, wherein 'L' is a distance between centers of holes in said plurality.

13. The method of claim 11, wherein individual holes of said plurality have a diameter that is greater than $(2)^{1/2}*L/2$ or $L/(3)^{1/2}$, wherein 'L' is a distance between centers of holes in said plurality.

14. The method of claim 1, said removing in (e) includes removing said single layer below said metallic material at a time that is substantially the same as removing a lateral portion of said single layer.

15. The method of claim 1, wherein said metallic material comprises gold, silver or platinum.

16. The method of claim 1, wherein said removing in (e) includes removing said metallic material adjacent to said layer.

17. The method of claim 1, wherein said at least one second hole is horizontally adjacent to said first hole.

* * * * *

UNITED STATES PATENT AND TRADEMARK OFFICE
CERTIFICATE OF CORRECTION

PATENT NO. : 10,438,811 B1
APPLICATION NO. : 14/687856
DATED : October 8, 2019
INVENTOR(S) : Shuji Ikeda Page 1 of 1

It is certified that error appears in the above-identified patent and that said Letters Patent is hereby corrected as shown below:

On the Title Page

Item [71], Replace "Quantum Biosystems Inc., Osaka (JP)" with --Quantum Biosystems Inc., Tokyo (JP)--

Signed and Sealed this
Tenth Day of December, 2019

Andrei Iancu
*Director of the United States Patent and Trademark Office*